(12) United States Patent
White et al.

(10) Patent No.: US 7,777,505 B2
(45) Date of Patent: Aug. 17, 2010

(54) NANOPORE PLATFORMS FOR ION CHANNEL RECORDINGS AND SINGLE MOLECULE DETECTION AND ANALYSIS

(75) Inventors: Henry S. White, Salt Lake City, UT (US); Ryan J. White, Salt Lake City, UT (US); Eric N. Ervin, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 446 days.

(21) Appl. No.: 11/743,472

(22) Filed: May 2, 2007

(65) Prior Publication Data

US 2008/0218184 A1 Sep. 11, 2008

Related U.S. Application Data

(60) Provisional application No. 60/797,850, filed on May 5, 2006, provisional application No. 60/849,883, filed on Oct. 6, 2006, provisional application No. 60/919,694, filed on Mar. 23, 2007.

(51) Int. Cl.
*G01R 27/08* (2006.01)
*G01R 31/08* (2006.01)

(52) U.S. Cl. .................. 324/693; 324/713; 324/525

(58) Field of Classification Search .............. 324/693, 324/713, 525
See application file for complete search history.

(56) References Cited

U.S. PATENT DOCUMENTS

| | | | | |
|---|---|---|---|---|
| 7,201,836 B2 * | 4/2007 | Vogel et al. | ............ | 205/777.5 |
| 2005/0009004 A1 | 1/2005 | Xu et al. | | |
| 2006/0063171 A1 * | 3/2006 | Akeson et al. | ............ | 435/6 |

OTHER PUBLICATIONS

Meller et al., "*Voltage-Driven DNA Translocations Through a Nanopore*", Physical Review Letters, vol. 86, No. 15, Apr. 9, 2001, pp. 3435-3438.

Chrisey et al., "*Covalent Attachment of Synthetic DNA to Self-Assembled Monolayer Films*", Nucleic Acids Research, vol. 24, Issue 15, 1996, abstract.

Deamer et al., "*Characterization of Nucleic Acids by Nanopore Analysis*", Accounts of Chemical Research, vol. 35. No. 10, 2002, pp. 817-825.

Kasianowicz et al., "*Characterization of Individual Polynucleotide Molecules Using a Membrane Channel*", Proc. Natl. Acad. Sci., vol. 93, Nov. 1996, pp. 13770-13773.

(Continued)

*Primary Examiner*—Amy He
(74) *Attorney, Agent, or Firm*—Diederiks & Whitelaw PLC

(57) ABSTRACT

A nanopore device includes a membrane having a nanopore extending there through forming a channel from a first side of the membrane to a second side of the membrane. The surface of the channel and first side of the membrane are modified with a hydrophobic coating. A first lipid monolayer is deposited on the first side of the membrane, and a second lipid monolayer is deposited on the second side of the membrane, wherein the hydrophobic coating causes spontaneous generation of a lipid bilayer across the nanopore orifice. Sensing entities, such as a protein ion channel, can be inserted and removed from the bilayer by adjusting transmembrane pressure, and adapter molecules can be electrostatically trapped in the ion channel by applying high transmembrane voltages, while resistance or current flow through the sensing entity can be measured electrically.

23 Claims, 18 Drawing Sheets

OTHER PUBLICATIONS

Molleman, "*Patch Clamping*", John Wiley & Sons, Ltd., ISBN: 0-471-48685-X, 2003.

Wayment et al., "*Controlling Binding Site Densities on Glass Surfaces*", Analytical Chemistry, vol. 78, No. 22, Nov. 2006, pp. 7841-7849.

White et al., "*Chapter 5, How to Set Up a Bilayer System*", The Physical Nature of Planar Bilayer Membranes in Ion Channel Reconstruction, Plenum Publishing Co., 1986, pp. 115-130.

Bayley et al., "*Stochastic Sensors Inspired by Biology*", Nature, vol. 413, Sep. 2001, pp. 226-230.

Song et al., "*Structure of Staphylococcal a-Hemolysin, a Heptameric Transmembrane Pore*", Science, vol. 273, Dec. 1996, pp. 1859-1866.

Wang et al., "*Electrostatic-Gated Transport in Chemically Modified Glass Nanopore Electrodes*", J. Am. Chem. Soc., vol. 128, 2006, pp. 7679-7686.

White et al., "*Ionic Conductivity of the Aqueous Layer Separating a Lipid Bilayer Membrane and a Glass Support*", Langmuir, vol. 22, 2006, pp. 10777-10783.

Zhang et al., "*The Nanopore Electrode*", Analytical Chemistry, vol. 76, No. 21, Nov. 2004, pp. 6229-6238.

Zhang et al., "*Steady-State Voltrammetric Response of the Nanopore Electrode*", Analytical Chemistry, vol. 78, No. 2, Jan. 2006, pp. 477-483.

\* cited by examiner

A.

AC

B.

DC

NANOPORE PLATFORMS FOR ION CHANNEL RECORDINGS AND SINGLE MOLECULE DETECTION AND ANALYSIS

CROSS-REFERENCE TO RELATED APPLICATIONS

This application claims the benefit under 35 U.S.C. §119 (e) of US Provisional Application No. 60/797,850, filed May 5, 2006, U.S. Provisional Application No. 60/849,883, filed Oct. 6, 2006, and U.S. Provisional Application No. 60/919, 694, filed Mar. 23, 2007, the entirety of each of which are incorporated by reference.

STATEMENT REGARDING FEDERALLY SPONSORED RESEARCH OR DEVELOPMENT

This invention was made with government support under grant #FA9550-06-C-0060 awarded by the Defense Advance Research Projects Agency. This invention was also made with government support under grant CHE-0616505 awarded by the National Science Foundation. The government has certain rights to this invention.

FIELD OF INVENTION

This invention relates to the field of nanotechnology, such as nano-sensors for ions, chemicals, bio-chemicals, and bio-molecules. In particular, the invention relates to nanopore platforms including lipid bilayers or similar polymer structures.

BACKGROUND OF INVENTION

The use of nanopores, including biological nanopores, for detection of single molecules has been in practice for two decades (Deamer, D. W. Branton, D., "Characterization of Nucleic Acids by Nanopore Analysis," Acc. Chem. Res. 2002, 35, 817-825). The biological protein nanopore α-hemolysin (αHL) from Staphylococcus aureus has proven to be ideal for single molecule detection, given the inner pore constriction diameter of ~1.4 nm (Song, S., Hobaugh, M. R., Shustak, C., Cheley, S., Bayley, H., Govaux, J. E., "Structure of Staphylococcal α-Hemolysin, a Hepatmeric Transmembrane Pore," Science, 1996, 274, 1859-1865).

By imbedding αHL into a lipid bilayer, the ionic resistance through the ion channel can be measured. αHL can be chemically modified or genetically engineered to selectively bind analyte molecules. Fluctuations in the resistance across a single channel can also be monitored as single molecules bind to the protein. These fluctuations are molecule specific allowing for the simultaneous detection and characterization of multiple analytes (Bayley, H, Cremer, P. S. "Stochastic Sensors Inspired by Biology," Nature, 2001, 413, 226-230)

Recently, the use of biological nanopores such as αHL for the detection and sequencing of DNA has been investigated (Kasianowicz, J. J., Brandin, E., Branton, D., Deamer, D. W., "Characterization of Individual Polynucleotide Molecules Using a Membrane Channel," Proc. Natl. Acad. Sci. 1996, 93, 13770-13773). Simple proof of concept experiments, where the number of nucleotides in the single stranded DNA (ss-DNA) was identified by measuring the length of time the strand spends in the ion channel, were conducted. By applying a small voltage, Deamer and coworkers were able to drive single DNA molecules through an ion channel that was inserted in a lipid bilayer. As the molecule translocates through the channel, a transient decrease in current is observed due to the DNA blocking the motion of the charge-carrying electrolyte ions.

Protein ion channel investigations rely on the formation of a lipid bilayer across a 15 μm to 150 μm diameter orifice in a thin TEFLON® or other polymer-based membrane. There are several drawbacks associated with this single-ion measurement platform due to the large area of the orifice. First, the lipid bilayer spanning the orifice of the Teflon or other polymer-based membrane is very susceptible to failure due to vibrations, pressure change and voltage fluctuations. Second, measurements in conventional bilayer systems indicate that the bilayer is not stable but in a state of continuous thinning. Even if extensive precautions are taken to minimize vibration and voltage disturbances, the bilayer lifetime is typically only a few hours. These robustness and lifetime problems are generally recognized as the key current roadblocks in developing usable sensors or sequencing devices based on protein ion channels, rule out and any type of portable or moveable system.

A more robust sensor platform capable of supporting the bilayer structure would expose a sub-microscopic bilayer region (e.g., 1 $\mu m^2$ or smaller area) for the insertion of a protein channel. The small area would reduce failures due to mechanical and electrical disturbances, and has been shown to allow lifetimes of greater than 20 days in preliminary tests. Such a device would allow for less complicated apparatus that does not require bulky and expensive vibration isolation, much longer duration operation, and potentially portable systems for applications of ion channels in drug development, biosensing, DNA sequencing, etc.

SUMMARY OF INVENTION

Provided is a nanopore device, the device comprising: a membrane having a thickness, having a first and second side, the first side being opposite to the second side, having a nanopore extending through the membrane over the thickness of the membrane, and a means that span across the nanopore on the first side of the membrane. The device may be used to detect a pore-forming entity by its action of being embedded in the means that span across the nanopore.

The device may further comprise a sensing entity, and the means that span across the nanopore may serve as a means for embedding the sensing entity. The device may further comprise a means for applying an electric field between the first side and the second side of the membrane; and a means for monitoring the current flow or resistance through the nanopore. Various embodiments of the nanopore device may be incorporated into large device structures that provide supporting elements for data acquisition and analysis.

In various embodiments of the invention, the membrane may be made of glass, Si, $SiO_2$, $Si_3N_4$, alumina, nitrides, metals, ceramics, polymers or other suitable materials. The membrane can be of a pure substance or a composite, or if necessary, comprises a coating that modifies the surface of the membrane. The thickness of the membrane is typically the smallest dimension of the membrane. The membrane ranges typically from about 10 μm to several hundreds of micrometers in thickness.

The nanopore device may further comprise a structure wherein the membrane is an integral part of the structure. For example, the nanopore device may comprise a chamber wherein the membrane is a part of the bottom or the side walls of the chamber. In a particular embodiment, a single nanopore is fabricated in a thin glass membrane which is part of the bottom wall of a glass capillary. In another particular embodiment, a single nanopore is fabricated in a quartz capillary.

The membrane may be configured to include more than one nanopore, or an array of nanopores. Each individual nanopore may be enclosed in an individual structure. For example, each individual nanopore may be enclosed in an individual chamber and such individual chambers may be arranged in an array format on suitable support structures.

In various embodiments, the nanopore has a first opening, a second opening, a length or depth, an interior surface and an exterior surface. The first surface of the membrane can be the exterior surface of the nanopore. The first opening opens to the first side of the membrane and the second opening opens to the second side of the membrane. Accordingly the nanopore forms a channel connecting the first and second side of the membrane. The two openings may be of different sizes or shapes. Preferably, the first opening is smaller than the second opening. In particular, the nanopore is of a truncated conical shape wherein the first opening is smaller the second opening. The radius of the first opening of the nanopore is preferably ranging from about 2 nm to about 500 nm, or larger. Radius of the second opening can be about 5 µm to 25 µm. Since the nanopore extends through the membrane and connects the first side and the second side of the membrane, the thickness of the membrane is typically the length or depth of the nanopore if the thickness of the membrane is uniform across the membrane. The length of the nanopore is preferably 20 times of the radius of the first opening of the nanopore. The length or depth of the nanopore may range from about 10 µm to hundreds of micrometers. The position of the nanopore may be located at any predetermined position on the membrane.

The sensing entity is capable of recognizing an analyte of interest. Such a sensing entity may be bait for nucleic acid in a mixture, a receptor for a hormone or small molecule messenger, an ion channel for an ion, an antigen for screening a library of antibodies, etc. The sensing entity may serve as the conductivity channel. The sensing entity may be an ion channel or other molecule-based conductive element engineered or modified to detect a specific chemical or biochemical analyte, or for sequencing nucleic acids.

The means that span across the nanopore on the first side of the membrane may comprise amphiphilic materials and/or polymeric materials that are deposited on the exterior and/or interior surface of the nanopore. Preferably, the means that span across the nanopore has a high resistance (1-100 GΩ). The amphiphilic materials may be a pure substance or a mixture of different amphiphilic materials. The polymeric materials may be a polymer with a uniform molecular weight distribution, or a polymer with a non-uniform molecular weight distribution, or a mixture of polymers which comprise different monomers. An amphiphilic molecule is essentially composed of two parts: a hydrophobic part and a polar part. Examples for amphiphilic molecules are lipids, detergents, surfactants, proteins, polysaccharides, and other chemical or biochemical materials that can be rendered amphiphilic. A lipid molecule typically comprises at least one hydrophobic chain and at least one polar head. Lipids, having various chain lengths or various structures of polar heads, can be used to form various structures on the membrane, for example, a monolayer, a bilayer of lipids or a combination of monolayer or bilayer on exterior and/or interior surface of the nanopore. Polymer layers, such as PDMS, that support functional ion channels and other molecule-based sensing transducers can also serve as a means that span across the nanopore.

In certain embodiments, the means that span across the nanopore is a lipid bilayer deposited on the exterior surface of the nanopore such that the lipid bilayer spans across the first opening of the nanopore. Such a lipid bilayer structure is termed as "supported lipid bilayer." There may be a thin layer (1-10 nm thick) containing solvent and ions formed between the lipid bilayer and the exterior space of the nanopore; the thickness of this layer is defined as the distance between the exterior surface and the lipid bilayer and is significant in determining the resistance of the bilayer seal and the stability and fluidity of the bilayer.

In certain embodiments, the means that span across the nanopore is a combination of a lipid bilayer and monolayer. In particular embodiments, a lipid monolayer deposited on the exterior surface of the nanopore and a lipid monolayer deposited on the interior surface of the nanopore that join together at about the edge of the first opening of a nanopore and thus forming a lipid bilayer spanning or suspended across the first opening of the nanopore. Such a means for embedding a sensing entity is termed as "spanning lipid bilayer" herein.

To effectively deposit the spanning bilayer structure for embedding the sensing entity, the exterior and/or interior surfaces of a nanopore may be modified by another suitable material, either physically or chemically, to change the surface properties, e.g., the electrical charge density, hydrophobicity or hydrophilicity, of the respective surfaces. The exterior surface of the nanopore may be modified by a first entity. The interior surface of the nanopore may be modified by a second entity. The first and the second entity may be the same entities. The first or second entities may be polymers, small organic molecules, proteins, etc. The modification of the surfaces may be physical or chemical in nature. For example, the first or second entity may be attached to the respective surfaces via noncovalent forces, for instance, by hydrophobic interactions. Alternatively, the first or second entity may be attached to the respective surfaces via covalent bonds.

In certain embodiments, to effectively deposit a lipid layer or bilayer on a glass membrane, the exterior and/or interior surface of the glass nanopore may be chemically modified to obtain a relatively more hydrophobic surface. For example, the glass surface may be modified by a variety of glass-reactive species, e.g., 3-cyano-propyldimethylchlorosilane, that reacts with the silanol groups of the glass surface. Changing the surface properties from that of bare glass, typically hydrophilic, to a moderately hydrophobic surface induces the hydrophobic part of a lipid molecule to point towards the surface when it is deposited on the surface. In particular, when the interior and exterior surfaces of a nanopore are rendered hydrophobic, deposition of a lipid monolayer on the glass surface spontaneously yields a bilayer across the first opening of the nanopore. That is, at the first opening of the pore, the lipid monolayer evolves into a lipid bilayer, while the lipids deposited on the exterior surface and interior surface still assume a monolayer structure. This transition between the lipid monolayer on the exterior surface and the lipid bilayer across the nanopore opening is a consequence of the chemical modification of the surfaces.

The lipid bilayer spanning (or supported) across the nanopore opening may serve as a means for embedding a sensing entity. Additionally, in the spanning lipid bilayer structure, the transition annulus region between the monolayer and the bilayer acts as a corral to pin the position of the sensing entity above the pore orifice preventing the diffusion of the sensing entity away form the pore opening. In the "supported lipid bilayer" structure, the sensing entity may or may not diffuse in the bilayer above both the pore opening and the support surface, depending on the structure and size of the sensing element, the interactions between the sensing element and the support surfaces, and depending of how the sensing element is inserted into the bilayer (i.e. from the solution facing the first or second side of the membrane support).

An applied electrical field means typically a first electrode being positioned on the first side of the nanopore membrane, and a second electrode being positioned on the second side of the nanopore membrane. The first and second electrode may be made of any suitable materials, such as, for example, Ag/AgCl. The first and the second electrode are usually positioned on the opposite side of the membrane. However, it is to be understood that positioning of the first and second electrode is relative in relation to the first and the second side of the membrane, or relative to the first opening and second opening of the nanopore. For example, if the second side of the membrane is enclosed in a chamber and the first side of the membrane is outside of the chamber, the first electrode is positioned outside the chamber, and the second electrode is positioned inside the chamber. The chamber may contain various suitable electrolytes, e.g., KCl.

In another aspect, the invention provides a method of forming a nanopore device, the method comprising: providing a membrane having a thickness, having a first side and a second side, and having a nanopore, which has a first opening, a second opening, an exterior surface and an interior surface, extending through the membrane over the thickness of the membrane wherein the first opening of the nanopore opens to the first side of the membrane; providing a means that spans across the first opening; providing a first electrode being positioned on the first side of the membrane and a second electrode being positioned on the second side of the membrane; and providing a means for monitoring the current flow or resistance through the nanopore.

The invention further provides a method of forming a nanopore device, the method comprising: providing a membrane having a thickness, having a first side and a second side, and having a nanopore, which has a first opening, a second opening, an exterior surface and an interior surface, extending through the membrane over the thickness of the membrane wherein the first opening of the nanopore opens to the first side of the membrane; providing a modified interior and exterior surface of the nanopore; providing a spanning lipid bilayer that spans across the first opening: providing a sensing entity embedded in the part of the lipid bilayer spanning across the first opening of the nanopore; providing a first electrode being positioned on the first side of the membrane ad a second electrode being positioned on the second side of the membrane; and providing a means for monitoring the current flow or resistance through the nanopore.

Further provided are methods of forming a nanopore device, such a method comprising: providing a membrane having a thickness, having a first side and a second side, and having a nanopore, which has a first opening, a second opening, an exterior surface and an interior surface, extending through the membrane over the thickness of the membrane wherein the first opening of the nanopore opens to the first side of the membrane; providing a supported lipid bilayer that spans across the first opening; providing a sensing entity embedded in the part of the lipid bilayer spanning across the first opening of the nanopore; providing a first electrode being positioned on the first side of the membrane and a second electrode being positioned on the second side of the membrane; and providing a means for monitoring the current flow or resistance through the nanopore.

In certain embodiments, the invention provides a method for single molecule detection of an analyte or for analysis of interactions between a sensing entity and an analyte, the method comprising: providing a sample solution containing an analyte of interest; providing a nanopore device including a sensing entity that recognizes the analyte; contacting the nanopore device with the solution such that the exterior surface of the nanopore is immersed in a solution and the interior nanopore surface is contacted by a solution, whether either solution contains the molecule or analyte of interest; applying an appropriate voltage across the two sides of the membrane; and analyzing the electrical conductivity to determine the concentration of the analyte of interest.

The analyte may be any entity that is recognizable by the sensing entity. Such analyte may include but are not limited to chemical or biological molecules, ions, polymers, lipids, particles, etc. When the sensing entity binds to the analyte, the binding event causes a reduction of current across the sensing entity. The current through the means sensing entity can be measured by using either alternating current (AC) or direct current (DC) measurements.

The invention provides a fundamental advantage in sensing and sequencing applications due to the very high mechanical and electrical stability of bilayers formed on the glass nanopore membranes. For instance, high electrical voltages (2 V on "supported lipid bilayer" and 0.75 V on "spanning lipid bilayer" structures) can be applied across the glass nanopore device with lipid bilayer supported ion channels as the sensing entity, allowing applications not assessable using conventional ion channel recording cells (~0.24 V limit). The mechanical stability allows devices with lipid bilayer supported ion channels to be transported. The combination of the very high mechanical and electrical stability of bilayers formed on the glass nanopore membranes greatly extends the lifetime of the devices in numerous applications.

Due to the unusually high voltage stability of the bilayer on the glass nanopore membrane, the invention provides a means to electrostatically trap molecules with charge and dipole groups within the channel of a protein that is supported within the lipid bilayer. For instance, an ionic adapter molecule used for enhancing chemical sensing applications of αHL can be electrostatically driven into the protein channel where it remains bound for indefinite periods of time. This ability is specifically applicable to strategies based on the nanopore membranes for chemical sensing and DNA sequencing using ion channels devices, due to the high voltage stability of the bilayer supported on the nanopore membrane.

The invention also provides a fundamental advantage in sensing and sequencing applications due to several orders of magnitude reduction in the bilayer area that spans the orifice of the nanopore. The reduction in bilayer area is accompanied by a proportional decrease in the bilayer capacitance (e.g., as much as a factor of $10^6$).

In certain embodiments, a modified glass nanopore corrals a single protein ion channel as the sensing entity, for instance, α-hemolysin (αHL), in the lipid bilayer region that spans the glass nanopore opening. The bilayer structure spanning over the modified glass nanopore is such that current can only flow through the protein ion channel. The protein ion channel is able to diffuse in the bilayer above the pore opening but cannot leave this area to enter the lipid monolayer. While an analyte is recognized by the ion channel and/or passes through ("translocates") the ion channel, it partially blocks ionic current through the pore. This blockade is measured by a transient increase in ionic resistance (or decrease in ionic current). The binding rate of the analyte may provide concentration of the analyte and/or affinity data of the analyte with the sensing entity.

In certain embodiments, the transmembrane pressure is used to control the rate of which protein ion channels are inserted and removed from the lipid bilayers deposited on the glass nanopore membrane. The pressure can be used to control the number of ion channels (single vs multiple channels), and to insert/remove channels at pre-selected times. This ability allows different protein ion channels to be inserted at different locations in a nanopore-based array sensor when placed in contact with a common solution, or sequentially with time in different solutions.

In certain embodiments, the invention provides a method for drug screening, the method comprising: providing a sample solution containing a drug candidate; providing a nanopore device including a sensing entity that is a drug target or a modified drug target; contacting the nanopore device with the solution such that the exterior surface of the nanopore is immersed in the solution and the nanopore is filled with the solution; applying an appropriate voltage across the two sides of the membrane; and analyzing the electrical conductivity to determine whether an interaction occurs between the drug target and the drug candidate and/or the affinity of the drug candidate with the drug target.

In certain embodiments, the invention provides a method for nucleic acid sequencing, the method comprising: providing a sample solution containing a DNA or RNA species; providing a nanopore device including a sensing entity that recognizes the identity of specific nucleotides; contacting the nanopore device with the solution such that the exterior surface of the nanopore is immersed in the solution and the nanopore is filled with the solution; applying an appropriate voltage across the two sides of the membrane; and analyzing the electrical conductivity to determine sequence of the DNA or RNA molecule. For example, as a DNA molecule passes through the protein ion channel included in a nanopore sensing device, a characteristic change in the ion channel conductance is associated with different nucleotides. By monitoring the time dependent conductance of the protein as the DNA passes through it, the nanopore sensing device may sequence a strand of DNA from just a couple bases in length up to hundreds of thousands bases in length.

In certain embodiments, the invention provides a method for detection of a pore-forming entity, the method comprising: providing a sample solution that may contain a pore-forming entity; providing a nanopore device that includes a means that span across the nanopore but does not include a sensing entity; contacting the nanopore device with the solution such that the exterior surface of the nanopore is immersed in the solution and the nanopore is filled with the solution; applying an appropriate voltage across the two sides of the membrane; and analyzing the electrical conductivity to determine whether the pore-forming entity is present in the solution and/or the amount of the pore-forming entity in the solution. Presence of a pore-forming entity increases the electrical conductivity across the two sides of the nanopore.

DESCRIPTION OF THE FIGURES

FIG. 9(B) shows i-t traces of $s_7\beta CD$ binding events with α-HL in solutions containing 25, 75, and 125 μM $s_7\beta CD$, respectively. Essentially identical recordings are obtained when the αHL is placed in the outside solution and the $s_7\beta CD$ is contained in the inside solution. "WT" in the figure corresponds to "wild-type" αHL. Mutant αHL channels function equally well using the glass nanopore membrane as the support.

FIG. 14(B) is a plot of the rate of αHL insertion as a function of transmembrane pressure for different size glass nanopore orifices.

FIG. 15(B) schematically depicts how the area of the bilayer decreases with decreasing transmembrane pressure and increases with increasing transmembrane pressure.

DETAILED DESCRIPTION OF THE INVENTION

Provided is a nanopore device for single-molecule detection, DNA sequencing, drug screening or other suitable applications, and preparation and use thereof. An advantage for such a nanopore device is that the device is very stable to mechanical vibrations and electrical disturbances allowing the sensing entity to be employed in the field or as part of an implantable medical device. A second advantage is that experiments show that bilayer membranes formed over nanoscale orifices are stable and do not undergo the continuous flow processes that limit the lifetime of bilayers on conventional TEFLON® supports. A third advantage is that an externally applied pressure can be used to control ion channel insertion and removal. A fourth advantage is that an increased bias voltage can be applied across the membrane to improve the measurement accuracy. A fifth advantage is that the capacitance of the bilayer region over the orifice is reduced to a negligible value, thereby reducing the shunt impedance in parallel with the ion channel. A sixth advantage is that an array of nanopores can be arranged in a miniaturized array for simultaneous detection of multiple analytes. The device can be used as a sensor for pharmaceutical industry, homeland security, environmental, and military applications and in the sequencing of nucleic acid, such as DNA.

Figure 1:
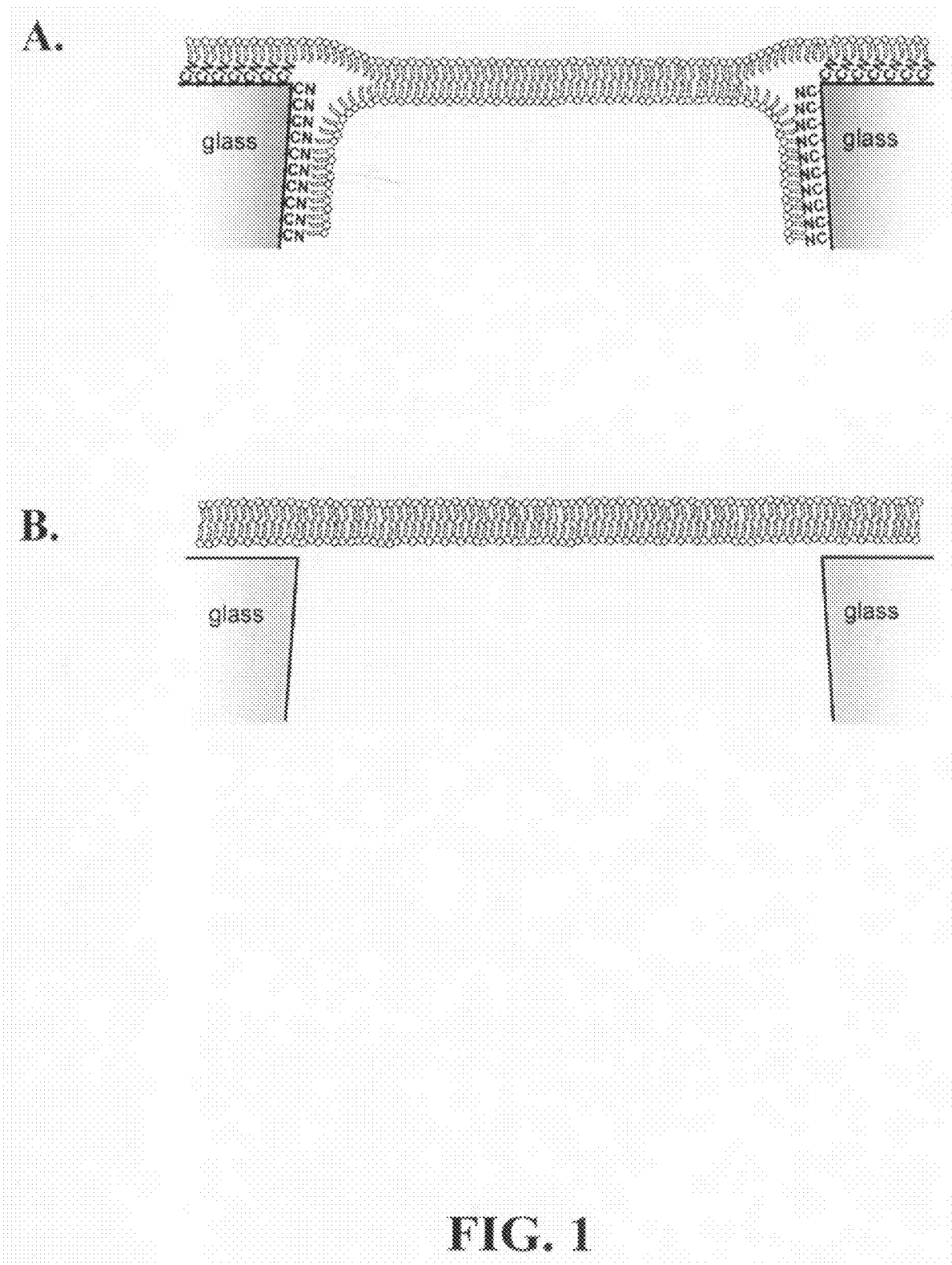
FIG. 1(A) is a schematic representation (cut away side view) of a lipid structure ("spanning lipid bilayer") deposited on a chemically modified glass nanopore.
FIG. 1(B) is a schematic representation (cut away side view) of a lipid structure deposited on a bare glass nanopore ("supported lipid bilayer").

FIG. 1(A) depicts a glass nanopore membrane with a spanning lipid bilayer. The exterior and interior surfaces of the membrane are chemically modified by a modifying agent that changes the surface properties from that of bare glass (hydrophilic) to a moderately hydrophobic surface. This change of surface property induces the hydrophobic tail groups of the lipid to point towards the surface when they are deposited. This chemical modification produces a lipid monolayer at the glass and spontaneously yields a bilayer across the first opening of the nanopore.

Figure 2:
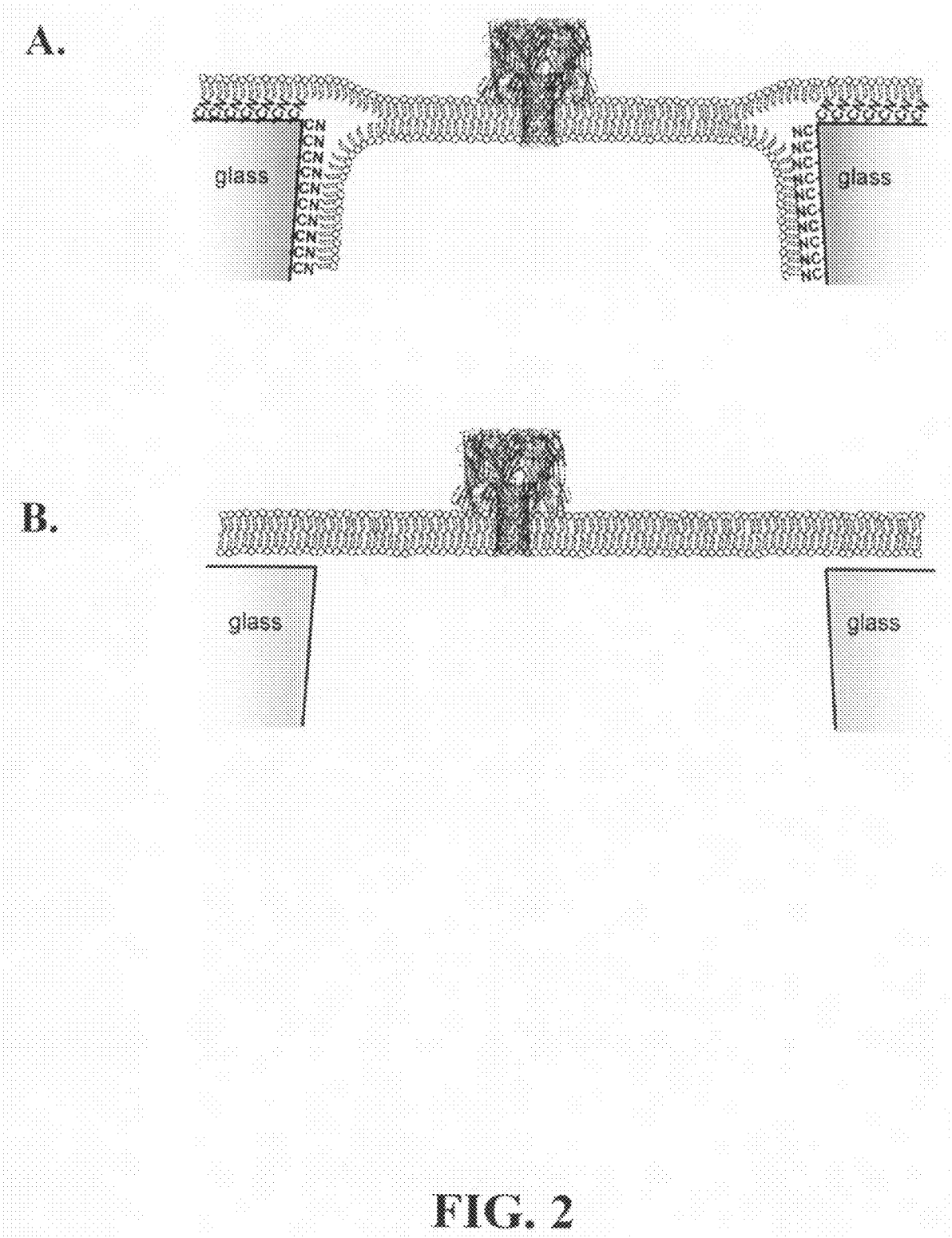
FIG. 2(A) is a schematic representation of a glass nanopore chemically modified with 3-cyanopropyldimethylchlorosilane, followed by deposition of lipids to form a spanning lipid bilayer, and insertion of an α-HL protein ion channel.
FIG. 2(B) is a schematic representation of a glass nanopore, following deposition of a supported lipid bilayer and insertion of an α-HL protein ion channel.

This transition between the lipid monolayer on glass and the lipid bilayer across the nanopore opening is a consequence of the chemical modification. One or more protein ion channels can be inserted into the bilayer (FIG. 2(A)) and used for single-molecule detection or DNA sequencing. For a nanopore fabricated in a glass capillary the protein ion channel may be inserted from the inside of the capillary or from the outside solution. Insertion from the inside of the capillary results in vertical inversion of the protein from the structure shown in FIG. 2(A).

FIG. 1(B) depicts a glass nanopore membrane with a supported lipid bilayer. The exterior and interior surfaces of the nanopore are not modified with a modifying agent. As shown in FIG. 1(B), a supported lipid bilayer is deposited on the exterior surface of the glass nanopore membrane (White, R. J., Zhang, B., Daniel. S., Tang, J. M., Ervin, E. N., Cremer, P. S., White, U S. "Ionic Conductivity of the Aqueous Layer Separating a Lipid Bilayer Membrane and a Glass Support," *Langmuir* 2006). In this case, the bilayer exists over the bare glass surface, as well as, over the first opening of the nanopore. A sensor molecule can be inserted anywhere where a bilayer exists over the exterior surface, FIG. 2(B), from the external solution in contact with the first opening of the pore or may be inserted from the internal solution in contact with the second opening of the pore. This structure is also suitable for measuring the fundamental properties of the aqueous layer that separates the lipid bilayer and the hydrophilic glass substrate (White, R. J., Zhang, B., Daniel, S., Tang, J. M., Ervin, E. N., Cremer, P. S., White, H. S. "Ionic Conductivity of the Aqueous Layer Separating a Lipid Bilayer Membrane and a Glass Support," *Langmuir,* 2006). The resulting supported bilayer-coated glass nanopore membrane as shown in FIGS. 1(B) and 2(B) as an ion channel platform for sensing applications is fundamentally different from the spanning bilayer-coated glass nanopore membrane as shown in FIGS. 1(A) and 2(A) for the following reasons: (1) the seal resistance between the bilayer and the glass is lower for the supported bilayer-coated glass nanopore membrane, which may preclude some applications, including DNA sequencing; (2) protein insertion from outside the capillary into supported bilayer occurs, but at a random distance from the pore opening; and (3) there is evidence that the proteins. e.g., αHL, adsorbs and denatures on bare glass surfaces. Surface modification of the glass, as in FIGS. 1(A) and 2(A), may reduce protein adsorption and denaturing (Wayment, J. R.; Harris, J. M., Controlling Binding Site Densities on Glass Surfaces, *Anal. Chem.;* 2006; 78; 7841-7849.).

As depicted in FIG. 2(B), the exterior and interior surface of a glass nanopore is chemically modified with 3-cyanopropyldimethylchlorosilane, followed by deposition of the lipid monolayer and bilayer (e.g., POPC, 1-Palmitoyl-2-Oleoyl-sn-Glycero-3-Phosphocholine or DPhPC, 1,2-Diphytanoyl-sn-Glycero-3-Phosphocholine,) by painting techniques or other suitable methods (e.g., tip-dip or Langmuir Blodgett deposition), and insertion of a single α-HL protein ion channel.

Figure 3:
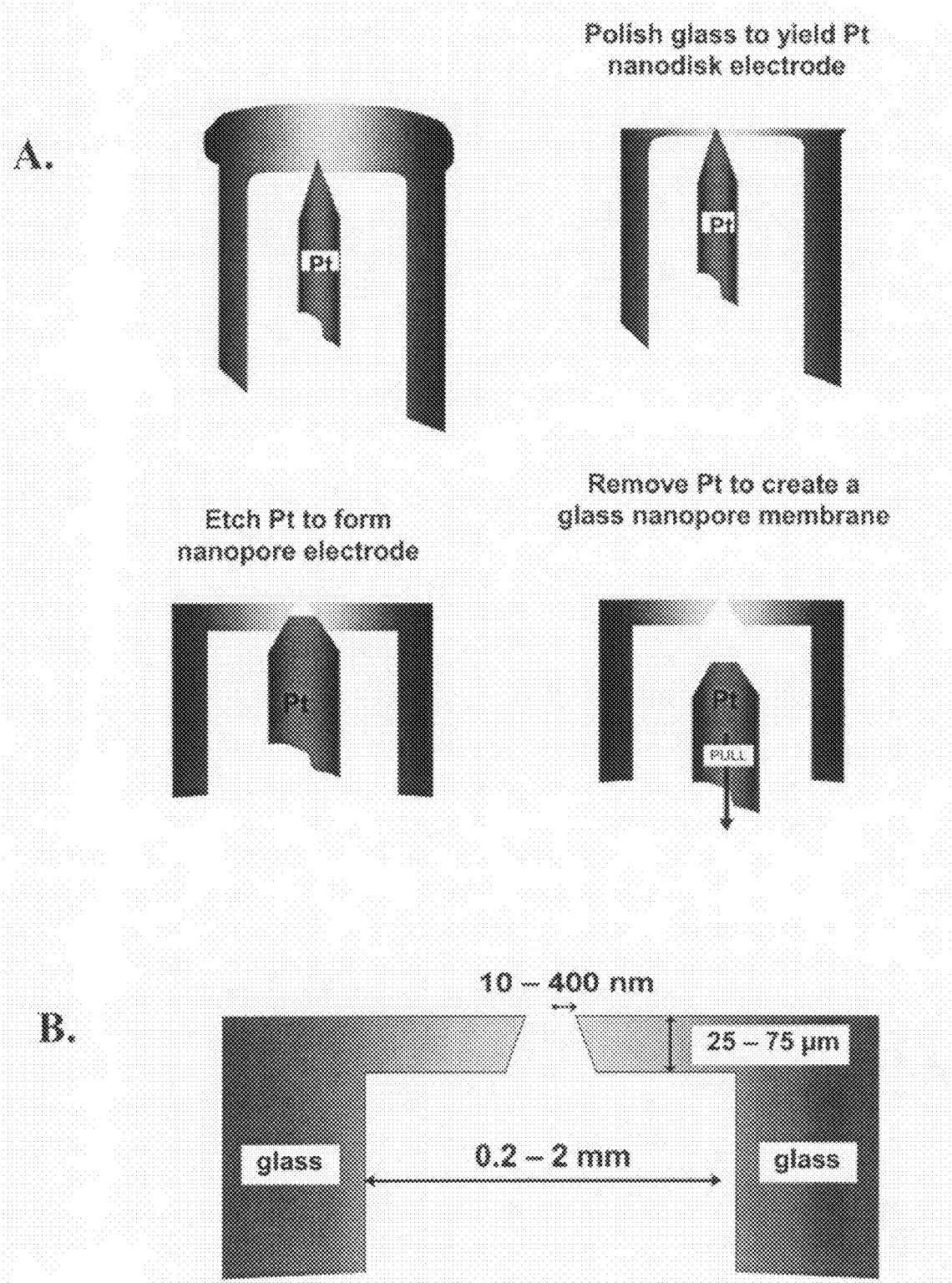
FIG. 3(A) schematically shows the general procedure for forming a glass nanopore membrane.
FIG. 3(B) shows dimensions of a preferred glass nanopore membrane.

In the above embodiments, the nanopore is fabricated in the membrane located at the end of a glass capillary as depicted in FIG. 3. A nanopore membrane may be prepared by the following procedures: (1) a nanopore template, for example, an atomically sharp metal tip is prepared and sealed in a substrate. (2) the substrate is polished in order to expose the tip of the template; (3) the exposed part of the template is etched to produce a nanopore in a substrate; and (4) the template is removed from the substrate to leave a nanopore in the substrate. Some fabrication methods of nanopores are disclosed in Bo Zhang, Yanhui Zhang, and Henry S. White, "The Nanopore Electrode," *Anal. Chem.,* 76, 6229-6238 (2004); Bo Zhang, Yanhui Zhang, and Henry S White, The Steady-State Voltammetric Response of the Nanopore Electrode, *Anal. Chem.* 78, 477-483 (2006); Ryan J. White, Bo Tang, Susan Daniel, John Tang, Eric N. Ervin, Paul S. Cremer, and Henry S. White, "Ionic Conductivity of the Aqueous Layer Separating a Lipid Bilayer Membrane and a Glass Support," *Langmuir*, 22, 10777-10783 (2006).)

The following provides an example of fabrication of a surface-modified glass nanopore membrane.

Glass nanopore membranes are fabricated by sealing 25-75 μm of an electrochemically etched Pt wire in a soda lime glass capillary (Bo Zhang et al. 2004; 2006). Next, glass is polished away while monitoring conductivity between the Pt and a wet polishing surface to expose a nanometer size Pt disk electrode shrouded in glass. The Pt is then removed from the glass to yield a conical-shaped nanopore. The size of the pore orifice can be characterized by measuring the ionic resistance (R. J. White et al., 2006). The glass surface of the glass nanopore membrane is silanized using with 3-cyanopropyldimethylchlorosilane (Wang, G.; Zhang, B.; Wayment, J. R.; Harris, J. M.; White, H. S., *J. Am. Chem. Soc.* 2006, 128, 7679-7686.).

Figure 4:
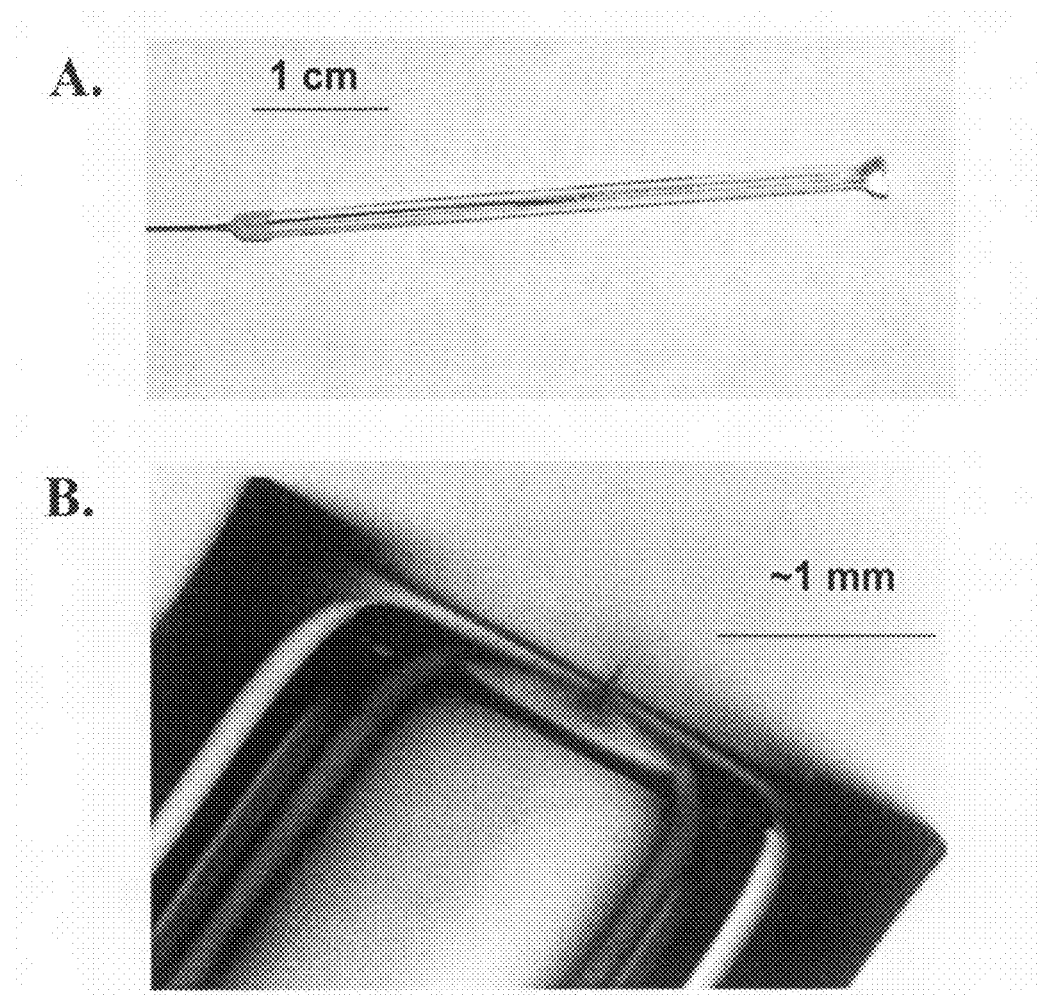
FIG. 4 shows optical images of (A) a glass capillary, and (B) the end of the capillary (magnified) showing the pore in the glass membrane.

FIG. 4 (A) shows a photograph of the glass capillary and FIG. 4 (B) shows a magnified view of the glass nanopore membrane. The first opening of the nanopore typically ranges from 10 and 500 nm (FIG. 3(B)), but the surface chemistry and preparation of the lipid bilayer apply to pores of larger and smaller sizes as well.

The spanning lipid bilayer nanopore device as depicted in FIGS. 1(A) and 2(A) has a number of advantages over the supported bilayer nanopore device (FIGS. 1(B) and 2(B)), but either can serve as stable suitable supports of ion channel sensing devices. First, in comparison to bare glass, the seal resistance between the silanized glass and the lipid bilayer is significantly larger (~5 relative to ~100 Gohms). This increase in resistance is a consequence of the lipid monolayer-to-bilayer transition near the pore circumference. Second, in either the supported or spanning bilayer structures, a sensing entity is readily inserted into the bilayer region from either side of the nanopore membrane. In the spanning bilayer structure, the bilayer is only present across the first opening of the nanopore and a monolayer is present on the chemically modified glass surface. The chemically modified glass nanopore thus corrals a single protein ion channel in the lipid bilayer region that spans across the glass nanopore. The protein ion channel is able to diffuse in the bilayer above the pore opening but cannot leave this area to enter the lipid monolayer. Insertion of the sensing entity only occurs in the bilayer region, confined within the bilayer, providing an optimal response. Third, adsorption/denaturing of a protein sensing entity are less likely to occur after the silanization reaction. Fourth, although the device as depicted in FIG. 2(A) behaves nearly identically to the conventional TEFLON®/black layer membrane system in terms of gating and molecule recognition, the device has vastly improved stability to mechanical vibrations and electrical disturbances, allowing the device to be employed in the field or as an implantable medical device.

Figure 6:
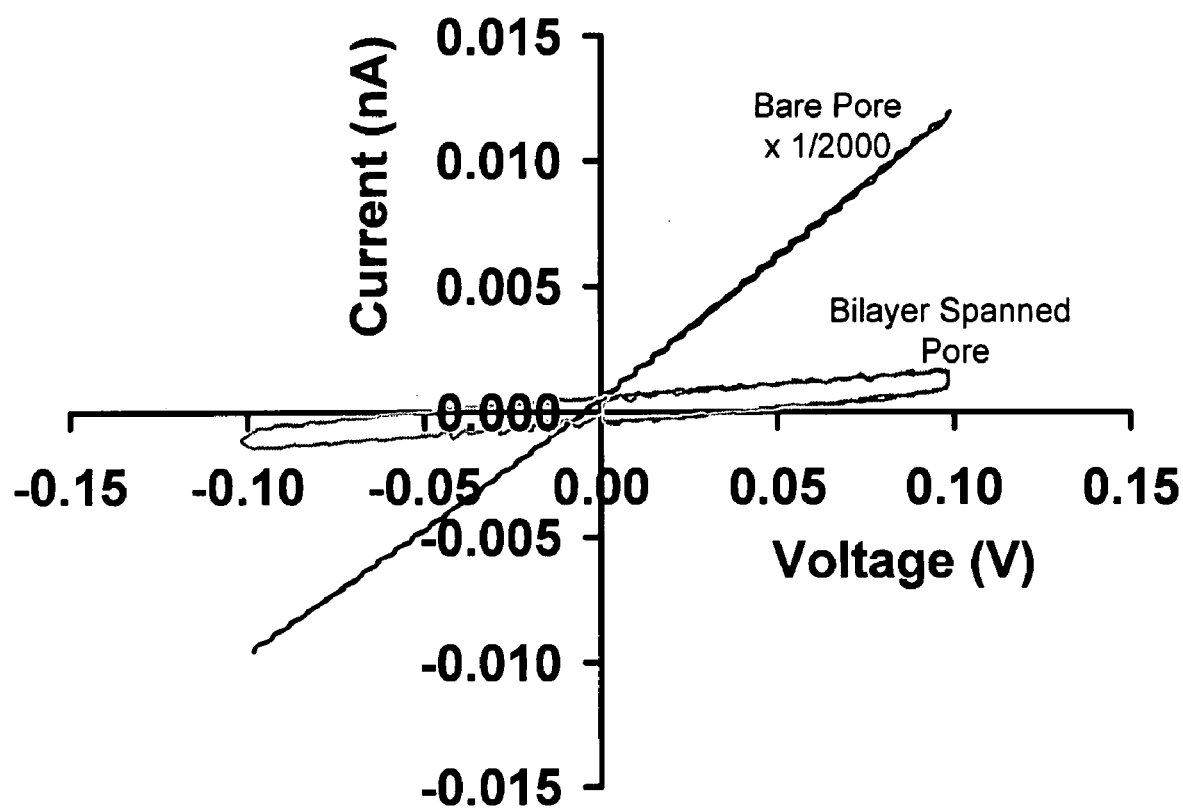
FIG. 6 shows i-V curves for a 150-nm-radius GNP in 1 M KCl 10 mM phosphate buffered saline (PBS) at pH 7.4. The bare-pore i-V curve is scaled by 1/2000 (labeled "Bare Pore") for comparison to the same structure ater POPC bilayer deposition across the orifice (labeled "Bilayer Spanned Pore"). The open-pore resistance and bilayer seal resistances are 1.26 MΩ and 88 GΩ, respectively.
Figure 7:
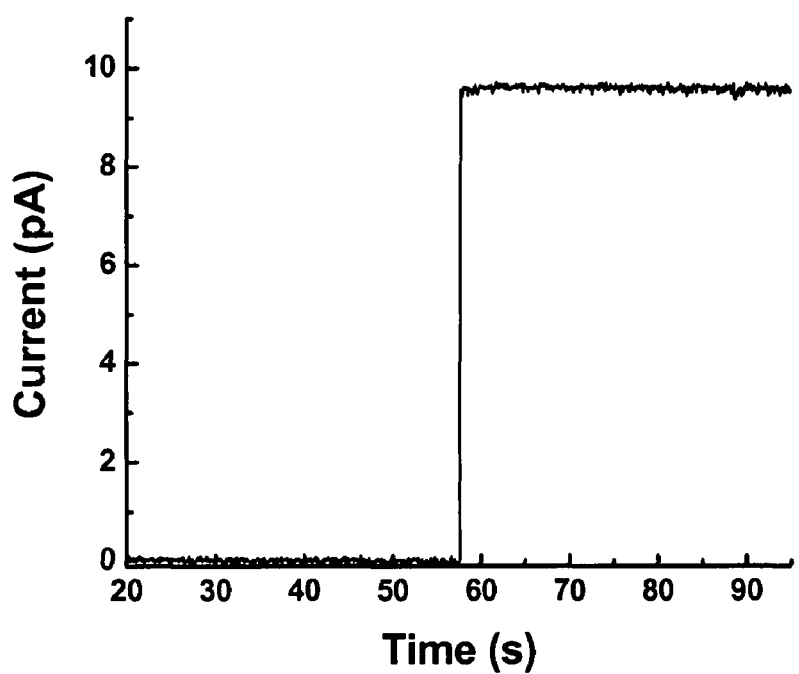
FIG. 7 are two graphs depicting AC (in the upper graph) and DC (in the lower graph) current-time recordings demonstrating the insertion of single ion channels (α-HL) into spanning lipid bilayers on GNP membranes (as depicted in FIG. 2(A)). The increase in current corresponds to the reported conductance of α-HL.
Figure 7:
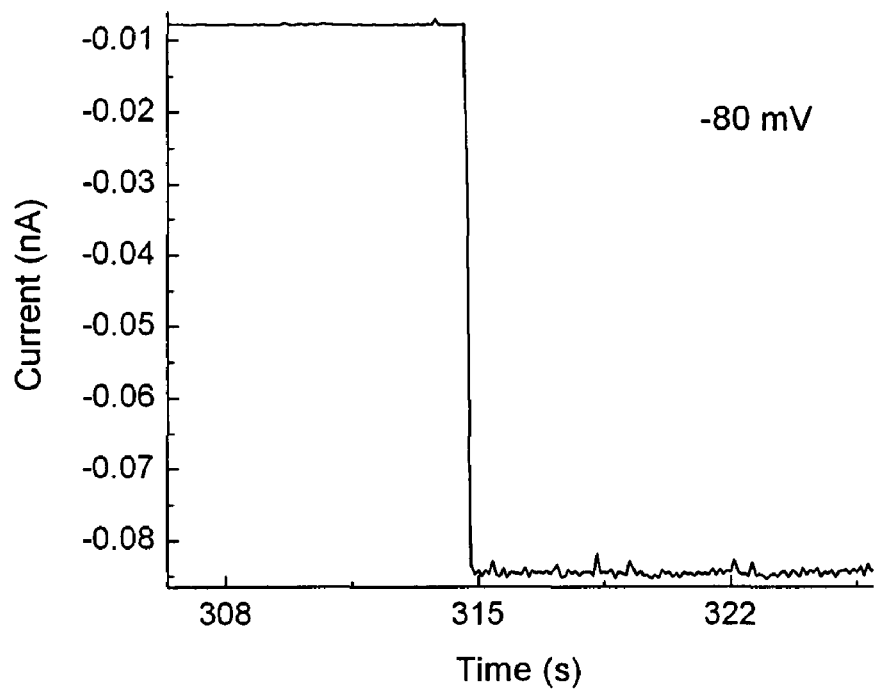

FIG. 6 is a graph showing current-voltage curves for a glass nanopore ("bare pore") and a glass nanopore after silanization and formation of the spanning bilayer structure ("bilayer spanned pore") demonstrating the high resistance of the bilayer seal obtainable with the spanning bilayer structure (FIG. 2(A)).

Figure 5:
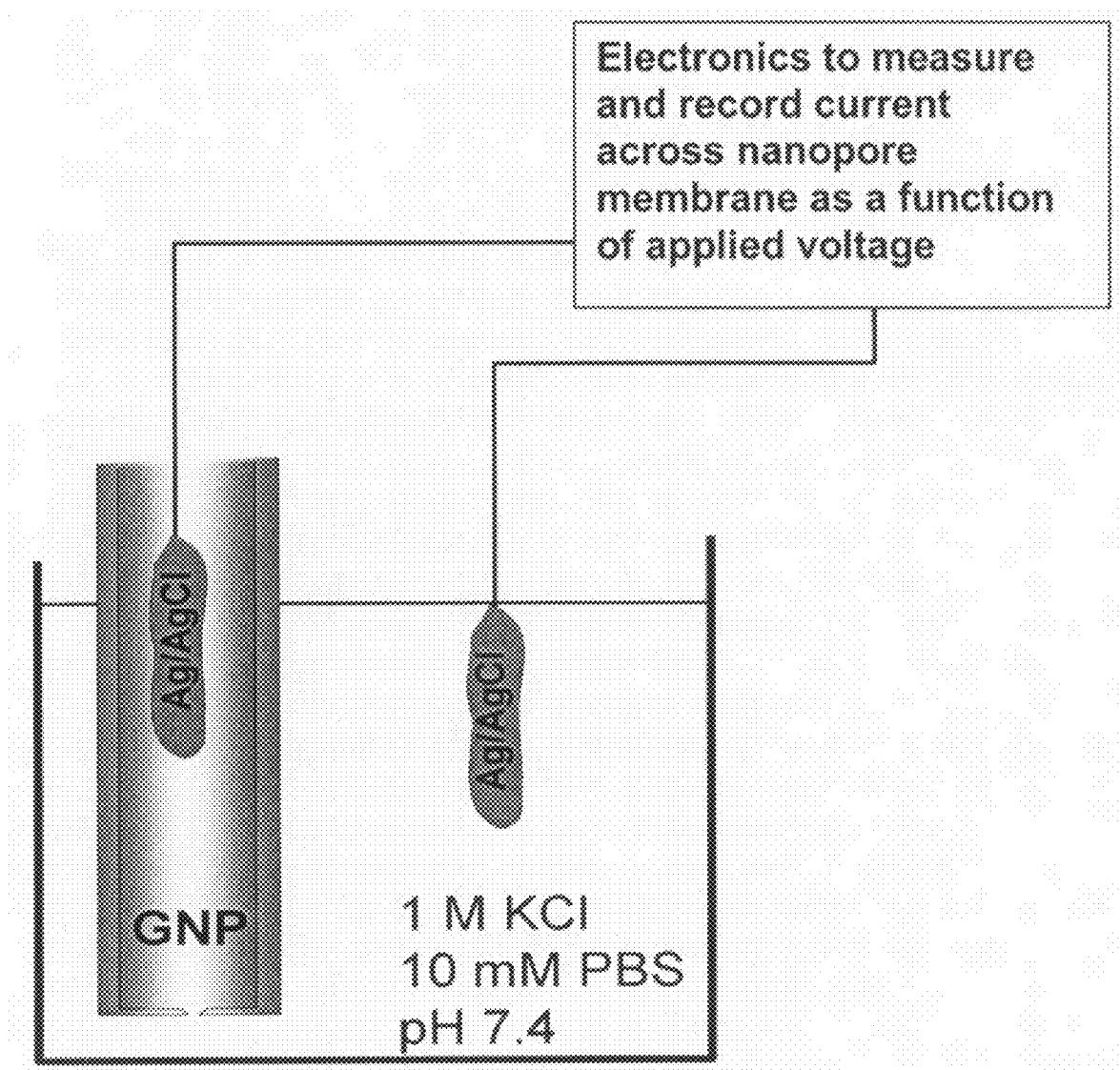
FIG. 5 depicts an experimental setup for using the GNP membrane in ion channel measurements. The lipid bilayer and ion channel are not shown.

The nanopore devices as depicted in FIGS. 2(A) and 2(B) have been used for single ion channel (αHL and outer membrane protein, ompF) measurements and stochastic single molecule detection of $s_7$-β-cyclodextrin ($s_7$·βCD) and DNA using the instrumentation depicted in FIG. 5.

In the embodiments associated with the graphs depicted in FIGS. 7-11, the current through the protein channel are measured by using AC or DC measurement between two Ag/AgCl electrodes located on the appropriate side of the glass membrane. Aqueous solutions containing an electrolyte to carry the current (e.g., KCl) are used throughout.

A nanopore device including a sensing entity detects an analyte by measuring the change in current or molecular flux within the nanopore when the analytic interacts (e.g., binds) or translocates through the sensing entity. For example, an analyte passes into the interior barrel of the αHL channel until it reaches the restriction zone (~1.4 nm). Wile the analyte is within the ion channel, it partially blocks ionic current through the pore. This blockade is measured by a transient increase in ionic resistance (or decrease in ionic current) measured either by AC or DC electrical methods, or a combination of the two. The DC voltage may be used to control the binding time or translocation rate of an analyte through the pore.

FIGS. 7A and 7B illustrate the capability of the chemically modified glass nanopore membrane as a support for single ion channel measurements. This figure shows current-time traces for the insertion of a single αHL into the bilayer spanning the opening of the nanopore. Both AC and DC current-time traces corresponding to this measurement are shown. Both methods yield ion channel conductance for αHL in agreement with the literature (~1.0 nS). The recordings are from two separate experiments. The AC measurement was performed using a small amplitude (10 mV) AC sine wave and phase sensitive detection of the current. The DC measurement was performed using a −80 mV DC voltage.

Figure 8:
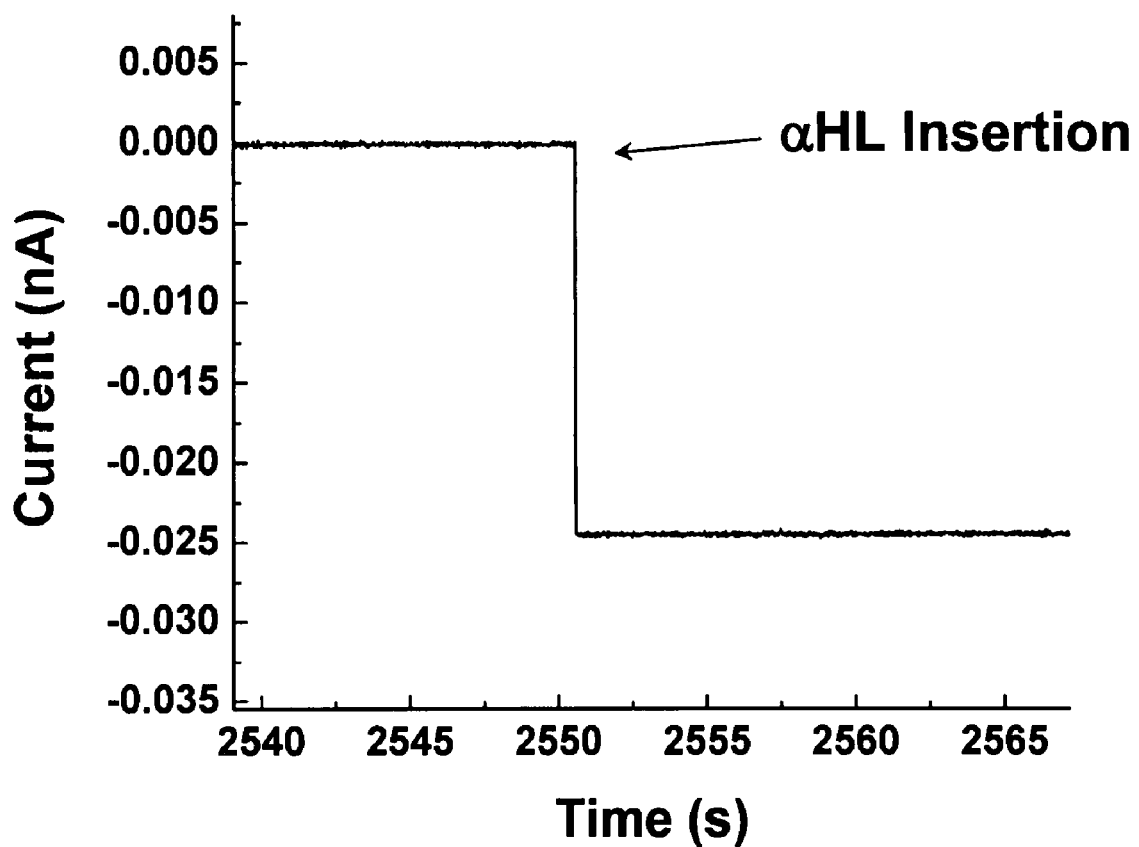
FIG. 8 depicts DC current-time recordings demonstrating the insertion of a single ion channel (α-HL) into a spanning lipid bilayer across the nanopore orifice of a membrane prepared from fused silica.

FIG. 8 is a graph depicting DC current-time recordings demonstrating the insertion of a single ion channel (α-HL) into a spanning lipid bilayer across a nanopore membrane prepared using fused silica instead of glass. Different glasses and silicates, for instance, Pb-doped or crown glasses, can be used instead of soda-lime glass, yielding identical bilayer structures (e.g., FIGS. 1-4), as well as similar behavior corresponding to bilayer formation, high resistant seals, and protein insertion (FIGS. 7-11). Pb-doped glass has higher resistance than soda-lime glass and thus devices prepared from these materials offer superior properties for ion channel recordings in some applications. Minor modifications of the nanopore membrane fabrication accompany the use of different membrane materials.

Figure 9:
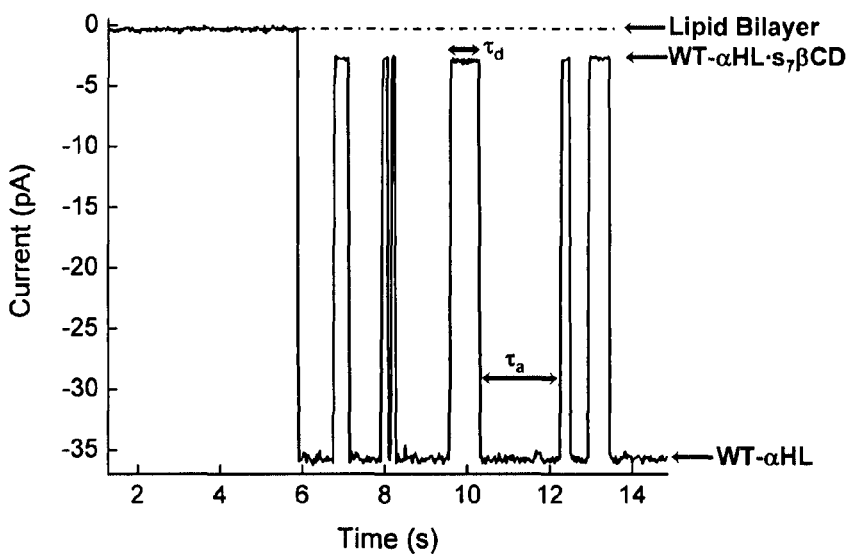
FIG. 9 (A) is an i-t trace of a baseline current corresponding to a spanning lipid bilayer structure (POPC) at a 250-nm-radius pore and the subsequent insertion of αHL at ~6 s at an applied DC bias of –40 mV. The single-channel conductance of the αHL channel is measured to be ~900 pS in 1 M KCl 10 mM PBS (pH 7.4). The solution inside the capillary contained 3 μM αHL, while the outside solution contained 100 μM [$s_7\beta CD$]. Labeled on the plot are the current levels for the bilayer alone, following a single αHL insertion, and the αHL·$s_7\beta CD$ complex. Binding dwell times, $\tau_d$, and the time between binding events, $\tau_a$, are labeled.
Figure 9:
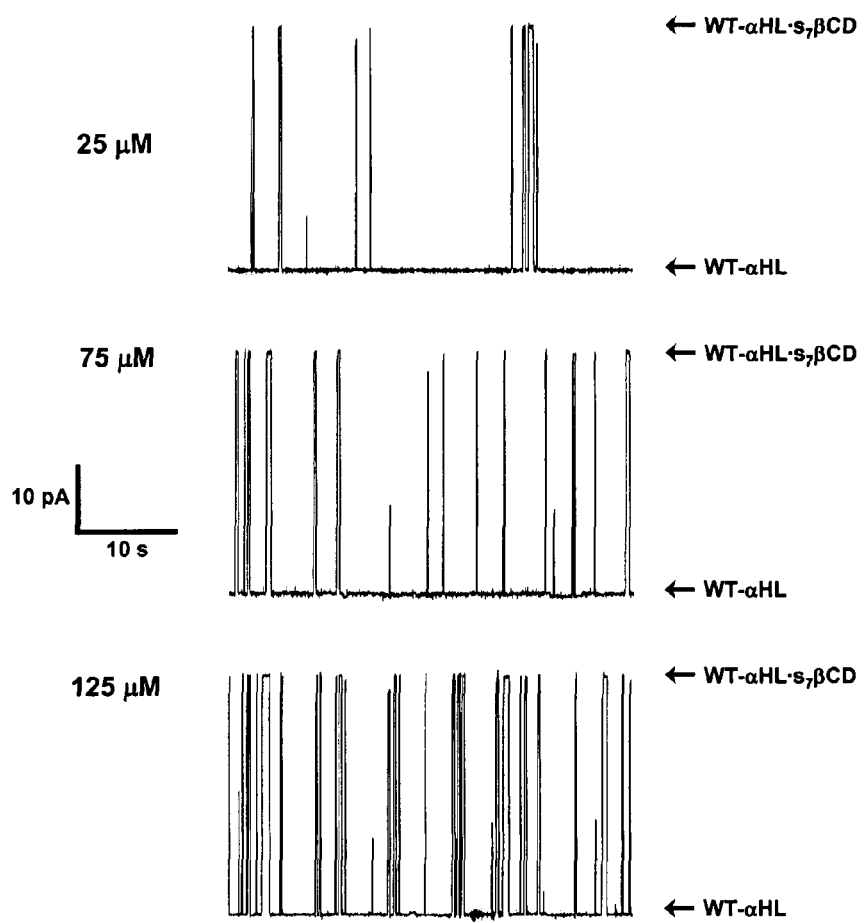
Figure 10:
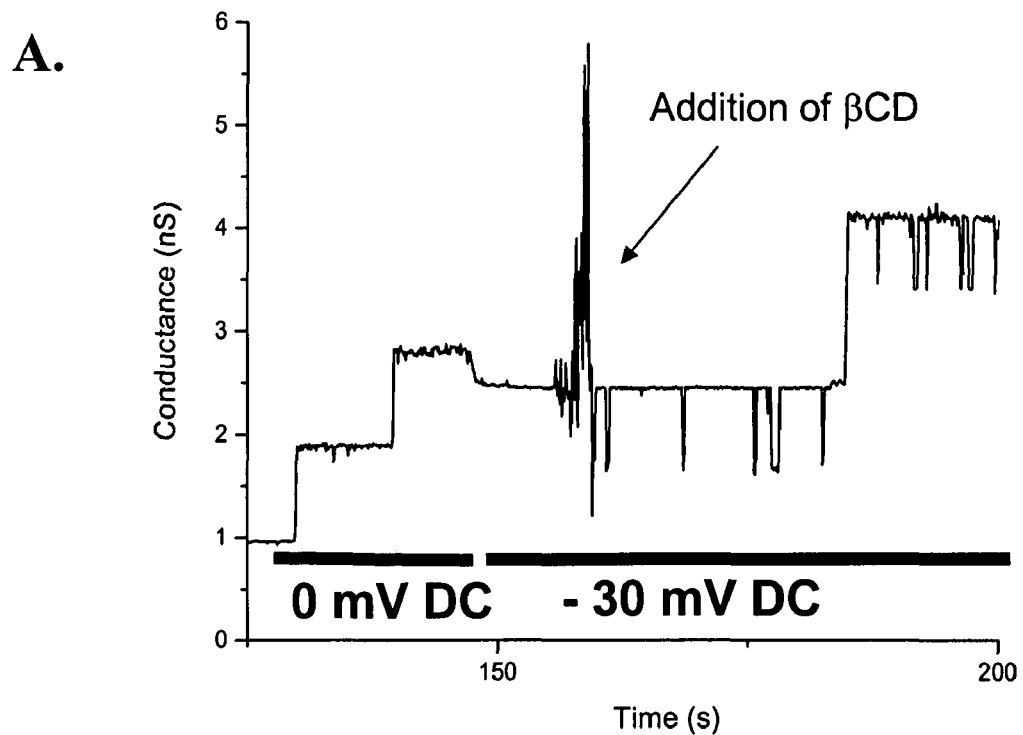
FIG. 10(A) (upper graph) shows AC i-t recordings obtained using phase-sensitive detection methods demonstrating single molecule detection of $s_7$ βCD by multiple αHL inserted into a spanning lipid bilayer on a GNP membrane (e.g., FIG. 2(A)).
FIG. 10(B) (lower graph) shows an expanded i-t trace of one blocking event.
Figure 10:
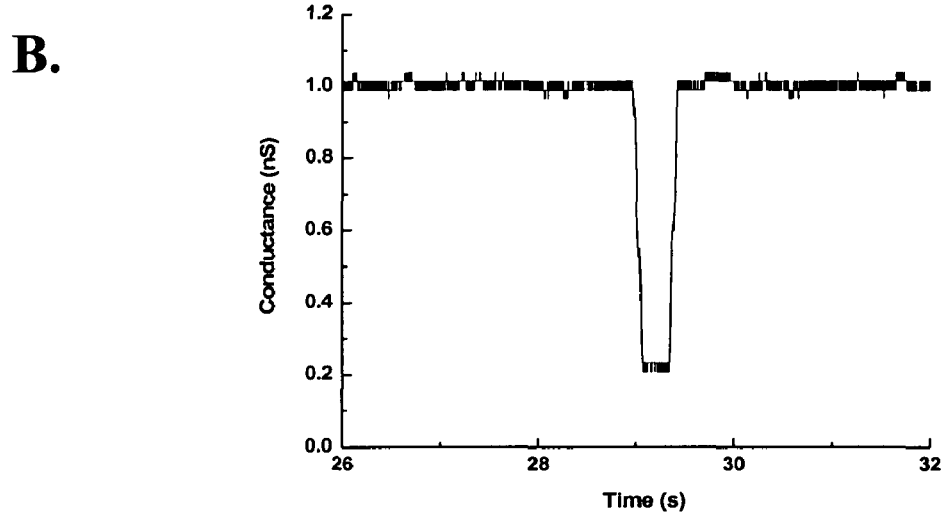

FIG. 9 are experimental results relating to an embodiment of the nanopore membrane devices for single molecule detection.

A glass capillary is placed in a solution comprising hepta-6-sulfato-β-cyclodextrin ($s_7$βCD), which is known to transiently bind αHL ion channel. One Ag/AgCl electrode is placed inside the glass capillary while the other electrode is placed outside of the capillary in the solution. The nanopore is of a truncated cone-shape. The first opening (smaller) is facing outside of the capillary and the second opening is facing the inside of the capillary. The radius of the first opening is 250 nm in this example. A spanning lipid bilayer is deposited across the first opening of the nanopore. After adding solution to the capillary, the back end of the capillary, i.e., the end opposite to the nanopore membrane, is sealed using a silicon rubber sealant after the Ag/AgCl electrode is placed inside of the glass capillary. This sealing increases the transmembrane pressure (the pressure across the bilayer, measured from inside the capillary vs the exterior solution), yielding a stable system in which the protein remains inserted within the bilayer. A superior method for controlling the pressure is described later.

For the experimental results shown in FIG. 9, the αHL ion channel is dissolved in the aqueous solution inside the capillary. A transmembrane potential of −40 mV is applied. At time=~6 s a change in the current corresponding to insertion of a single αHL channel is observed. The increase in ionic current corresponds to a conductance of ~1 nS which is in good agreement with reported literature values.

FIG. 9(A) also illustrates single binding events of $s_7\beta CD$ at the αHL ion channel embedded in the spanning lipid bilayer spanning across the nanopore. The characteristic times are indicated in FIG. 9(A) where the association time ($\tau_a$ (s)) is the time between each event, and the dissociation time ($\tau_d$(s)) is the time of each binding event. When $s_7\beta CD$ is bound, the conductance through the αHL is reduced by ~90%. The binding of $s_7\beta CD$ exhibits a dependence on concentration. FIG. 9(B) shows three different i-t plots of $s_7\beta CD$ detection in a single αHL channel embedded in a spanning lipid bilayer over a glass nanopore membrane with varying [$s_7\beta CD$] of 25 µM, 75 µM, and 125 µM. As the $s_7\beta CD$ concentration is increased, $\tau_a$ decreases.

αHL and ompF channels have been inserted into the lipid bilayer at the first opening (smaller pore opening) of the glass nanopore, from both the exterior and interior solutions, and $s_7\beta CD$ detected using αHL inserted from either side of the lipid bilayer. These results demonstrate the generality of ion channel recording using the nanopore membranes.

Single or multiple ion channel insertions may be obtained using the methods described above. A single ion channel insertion (i.e., without a second additional channel insertion) may be obtained by replacing the solution containing the protein channels, after the first insertion, with a solution in which the protein is absent. Multiple channel insertions (e.g., 5 to 10) occur over time if the device is left in contact with the protein solution.

FIG. 10(A) shows the AC conductance following insertion of 2 αHL channels without an applied DC bias, and the detection of $s_7 \cdot \beta CD$ using a −30 mV DC bias. In the latter case, a slight negative DC bias increases the counting rate of $s_7 \cdot \beta CD$ molecules, but is not necessary. Any combination of DC and AC can be used with the glass nanopore platform for ion channel measurements. The DC biased was changed at ~140 s to increase capture rate of $s_7$ βCD. The decrease in conductance when $s_7$ βCD binds to the channel is 70-80%, in agreement with ion channel measurements employing a TEFLON™ cell. The data also demonstrate the insertion of multiple αHL channels into the bilayer.

FIG. 10(B) shows a expanded i-t trace of a single blocking event corresponding to the detection of an individual molecule of $s_7 \cdot \beta CD$, recorded using AC detection.

Figure 11:
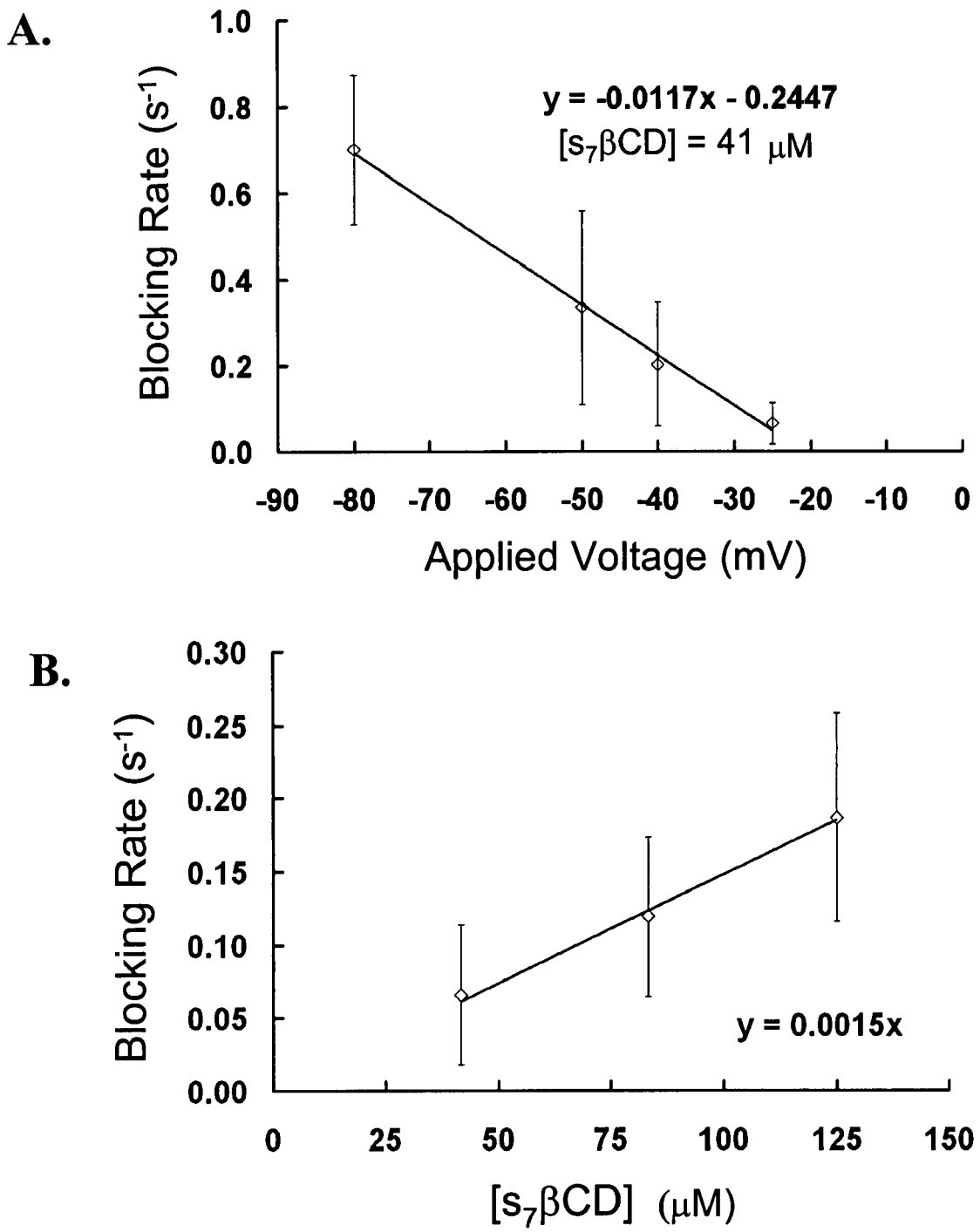
FIG. 11 are two graphs showing dependencies of blocking rate (single-molecule counts per second) on the applied DC bias (top graph) and bulk $s_7\beta CD$ concentration (bottom graph) using a single αHL ion channel embedded in a spanning lipid bilayer deposited on a chemically-modified glass nanopore.

FIGS. 11(A) and 11(B) are graphs showing the dependence of the counting rates for the detection of $s_7 \beta CD$ on the applied DC bias and the bulk concentration of $s_7 \cdot CD$. The ability to control the rate of $s_7 \cdot CD$ binding using DC voltage while measuring the count rate separately and simultaneously via AC detection, is demonstrated by the top panel in FIG. 11. The ability to use the chemically-modified glass nanopore supported bilayer and protein for analyte concentration measurements is demonstrated in the bottom panel of FIG. 11. The results demonstrate that the chemically-modified nanopore, with lipid and protein, is capable of measuring the analyte concentration, and that the sensitivity can be controlled by varying the DC bias, while recording the analyte binding events separately using AC methods.

Figure 12:
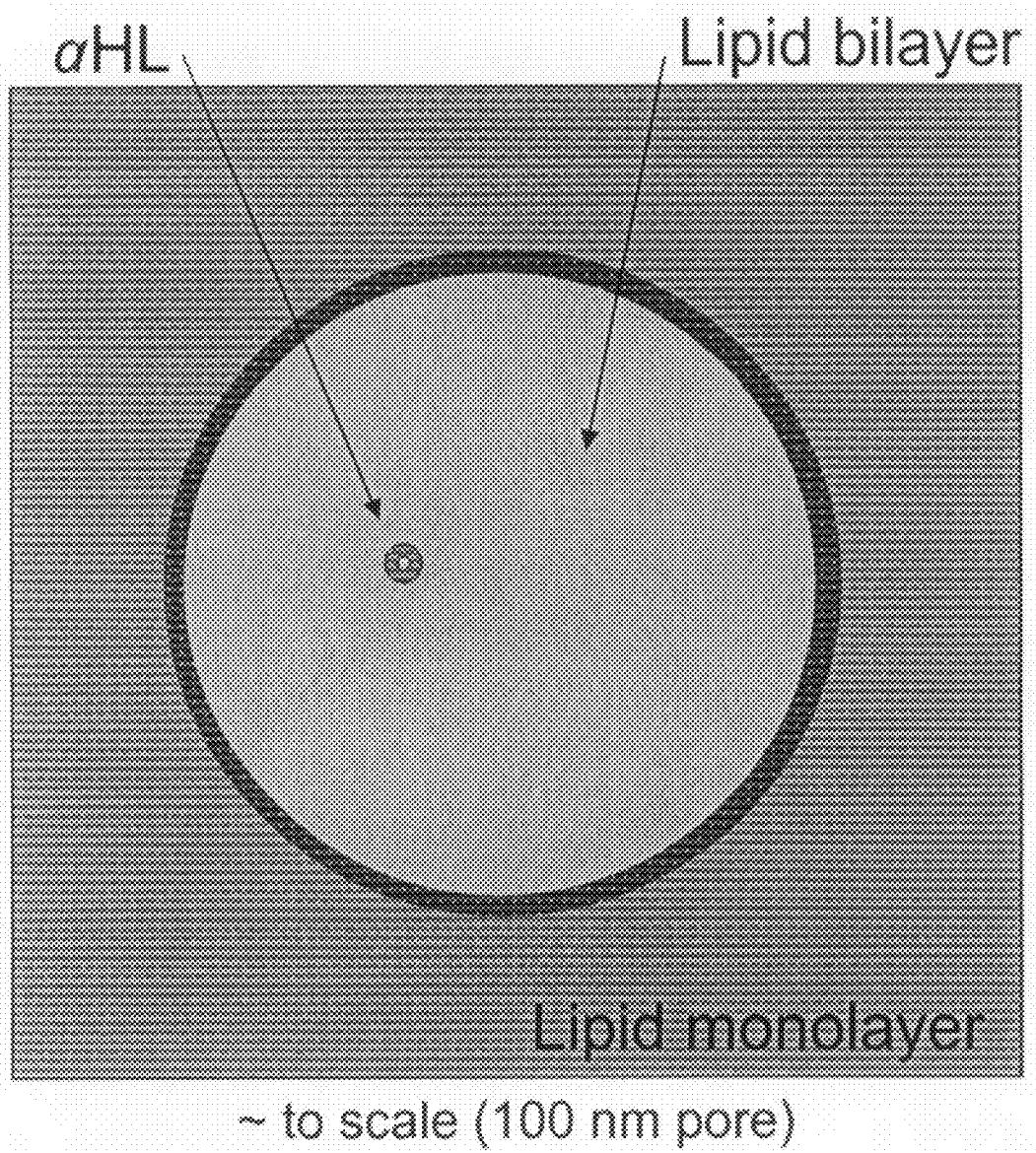
FIG. 12 schematically depicts a top-down view of a glass nanopore membrane orifice, the lipid monolayer on the top glass surface, the spanning lipid bilayer across the orifice, and a single αHL channel inserted into the bilayer.

The results embodied in FIGS. 7-11 demonstrate that the protein channel αHL is inserted in the lipid bilayer spanning the orifice of the glass nanopore membranes, and that the channel functions for ion channel recording, including the detection of single molecule events. Furthermore, the results indicate that the spanning lipid bilayer structure corrals the ion channel above the small opening of the nanopore membrane. A schematic drawing, drawn approximately to scale, of a top-down view of the small opening, lipid monolayer and bilayer, and a single αHL channel is shown in FIG. 12.

As noted earlier, a positive transmembrane pressure applied between the inside of the capillary and exterior solution increases the stability of the protein insertion. This can be accomplished by sealing the back end of the capillary with silicon rubber sealant after the capillary is filled with the appropriate solution. The sealing processes leads to an increase of the pressure inside the capillary relative to the exterior solution.

Figure 13:
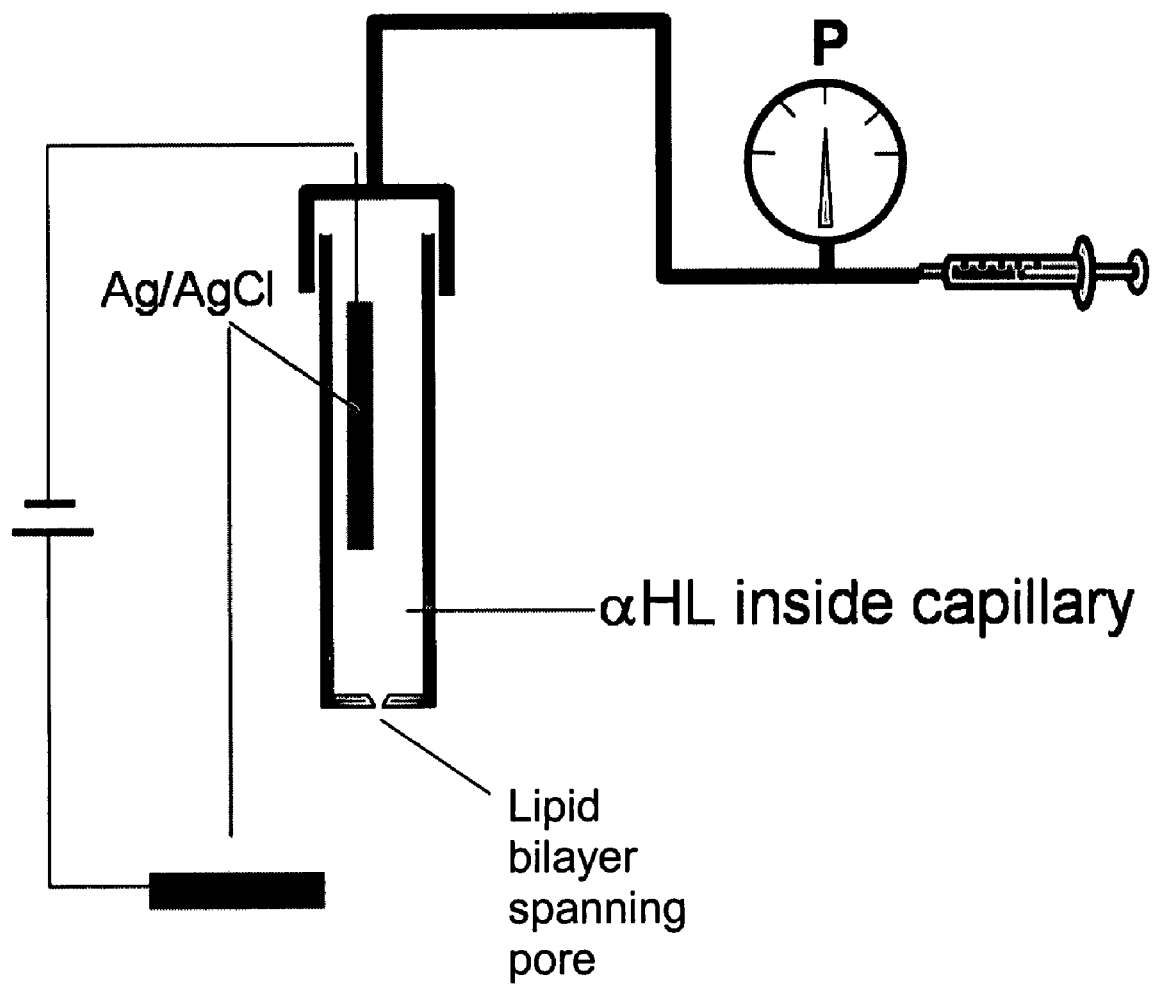
FIG. 13 schematically depicts the instrumentation to control and monitor the pressure across the lipid bilayer (pressure inside capillary vs outside solution pressure, referred to herein as "transmembrane pressure").

Transmembrane pressure can be used to control the rate of insertion and removal of αHL from the bilayer in a quantitative and predicable manner. The pressure rig shown in FIG. 13 can be used for this purpose. The experiment is performed by applying a pressure, ranging from −500 to 500 mm Hg, across the opening of the bilayer deposited on the nanopore membrane using a syringe or appropriate mechanical device to apply a pressure force on the solution inside the capillary. The air and aqueous solution inside the glass nanopore membrane are compressed yielding a transmembrane pressure that is monitored with a pressure gauge. For convention, positive pressure corresponds to a compression of the air and solution inside this capillary.

Figure 14:
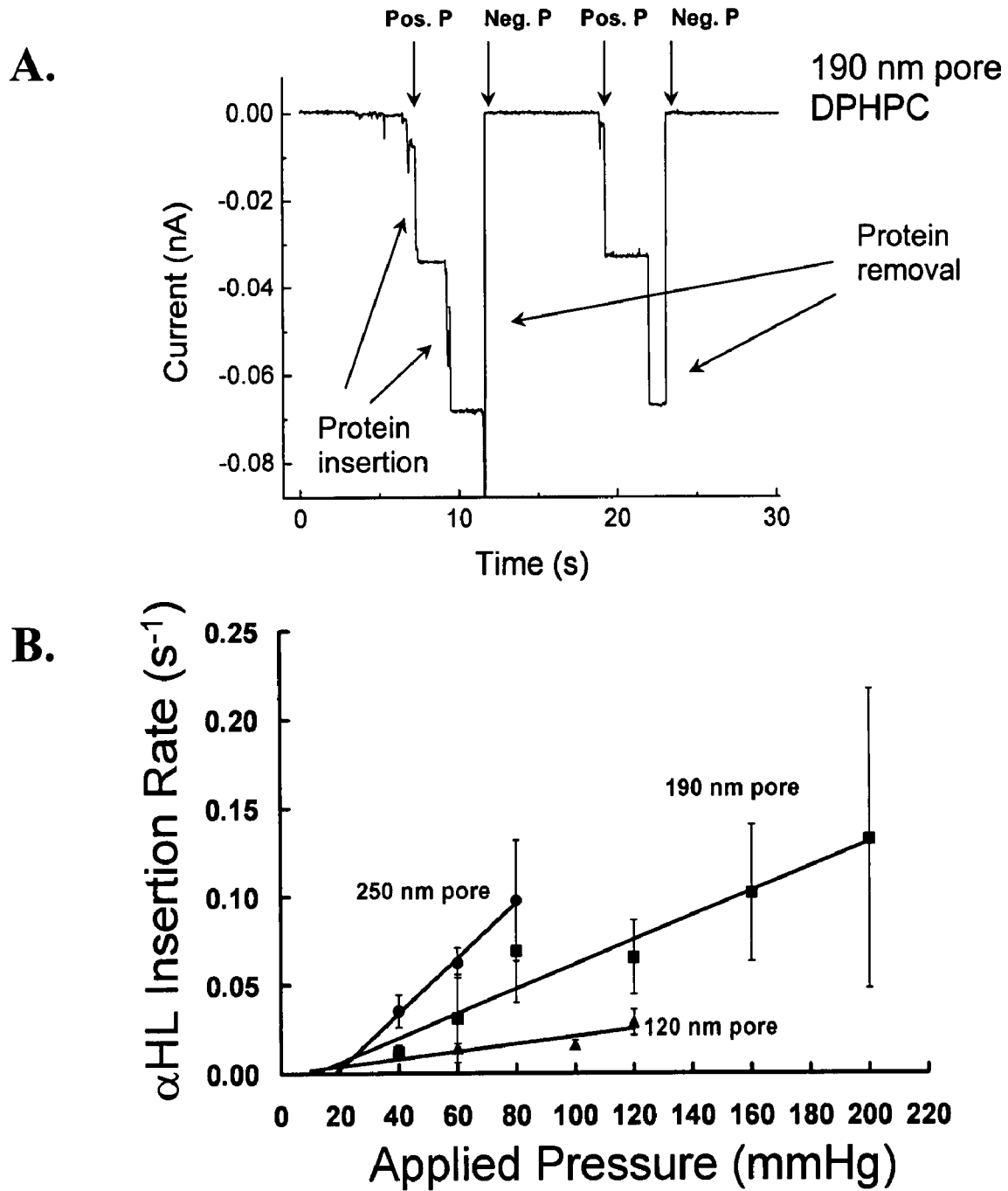
FIG. 14 (A) is an i-t trace showing the influence of transmembrane pressure on protein insertion and removal. A positive transmembrane pressure of >20 mm Hg (inside vs. outside solution) results in insertion of αHL channels. The channels are reversibly removed by reducing the pressure or applying a negative pressure.

FIG. 14(A) is an i-t plot of pressure-controlled experiments that illustrates qualitatively the ability to insert and remove the protein from the bilayer as a function of transmembrane pressure. At t=5 s, a positive pressure is applied to insert αHL insertion into the bilayer. At t=11 s, the pressure is switched from a positive pressure to a negative pressure which results in the sudden removal of all αHL channels in the bilayer membrane. The bilayer membrane remains intact once the protein channels are removed and the process of inserting and removing the protein ion channels can be repeated numerous times.

FIG. 14(B) shows the dependence of αHL insertion rate as a function of applied positive pressure, demonstrating quantitative control of the insertion rate as a function of pressure. Data are presented for three different glass nanopore membranes with small opening radii ranging from 120 to 250 nm. Insertion rates are larger for the larger nanopore openings as there is larger bilayer area for the protein to insert itself into.

To further understand this phenomenon, insertion of αHL as a function of applied pressure was studied with αHL in the front side solution rather than the back side. The results are qualitatively the same as when protein is inserted from the solution inside the capillary. This result shows that the pressure applied is not creating significant hydrodynamic flow; rather the pressure directly effects bilayer structure, making it more favorable for protein insertion when a positive transmembrane pressure is applied.

Figure 15:
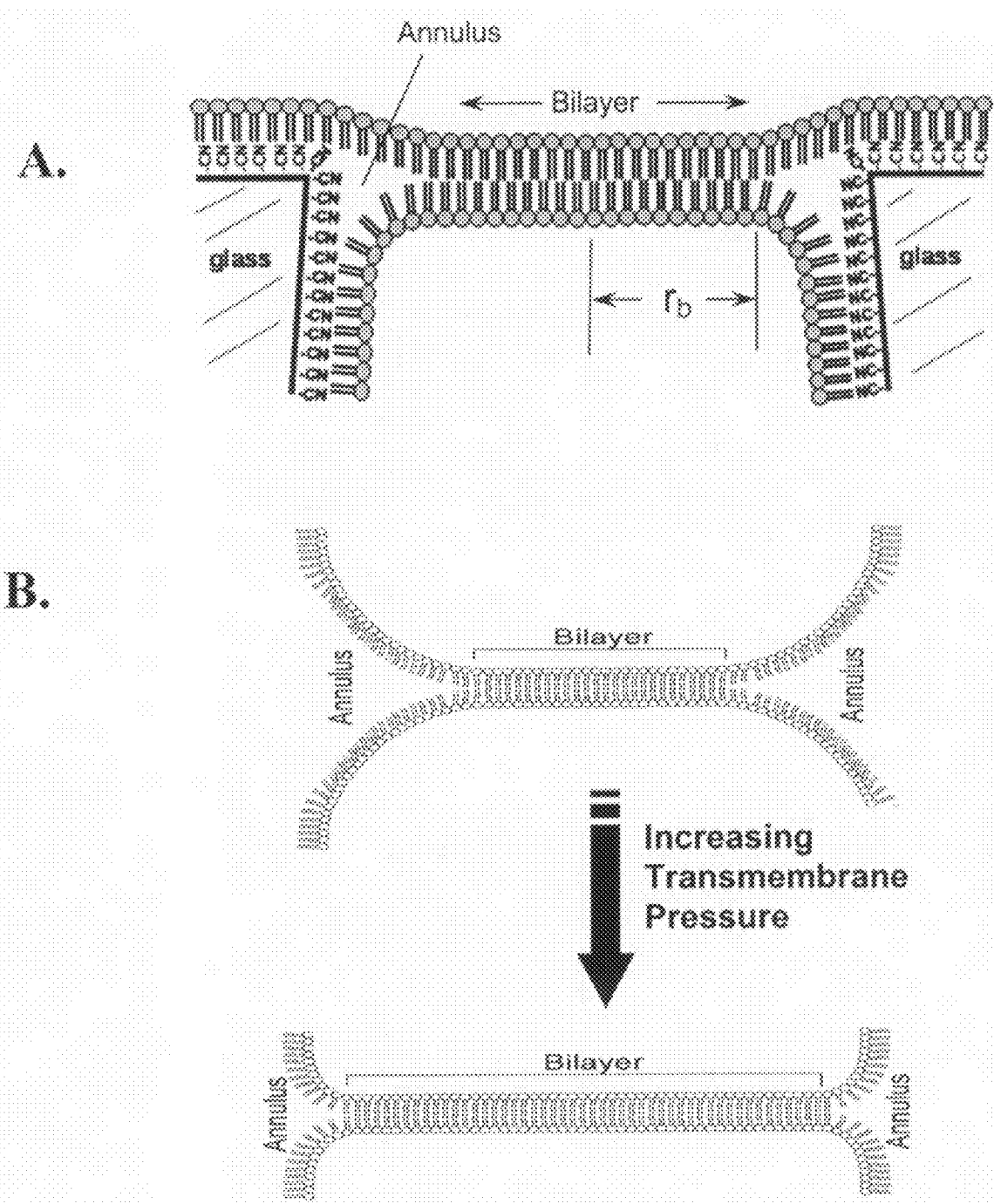
FIG. 15 (A) is a schematic (cut away side view) depicting the bilayer region, the annulus region at the edges of the bilayer near the glass surface, and the radius of the bilayer region, $r_b$.

It has been shown that the area of the bilayer film after painting over an TEFLON™ orifice with lipid/hydrocarbon solution is partially controlled by hydrostatic pressure differences described by Laplace's law: $\Delta P = 2\gamma / R$. Here γ is the interfacial tension, R is the radius of curvature, and $\Delta P$ is the hydrostatic pressure difference. (White, S. H. *The Physical Nature of Planar Bilayer Membranes* in Ion Channel Reconstitution; Miller, C.; Plenum Publishing Co., New York, 1986, 115-130). As the transmembrane pressure is increased, the radius of curvature decreases causing an increase in the area of bilayer for protein insertion. In FIG. 15A, the radius of the bilayer is indicated by the symbol ran. The value of $r_b$ increases with increasing pressure. As the area of the bilayer increases the probability of a αHL also increases, regardless of which side the protein inserts from. The geometrical asymmetry of the nanopore membrane results in a negative applied pressure not showing the same effect of the positive pressure.

The negative pressure results in an increase in the radius of curvature, decreasing the area where bilayer exists, thus causing the sudden removal of protein as shown in FIG. 15(B).

Figure 16:
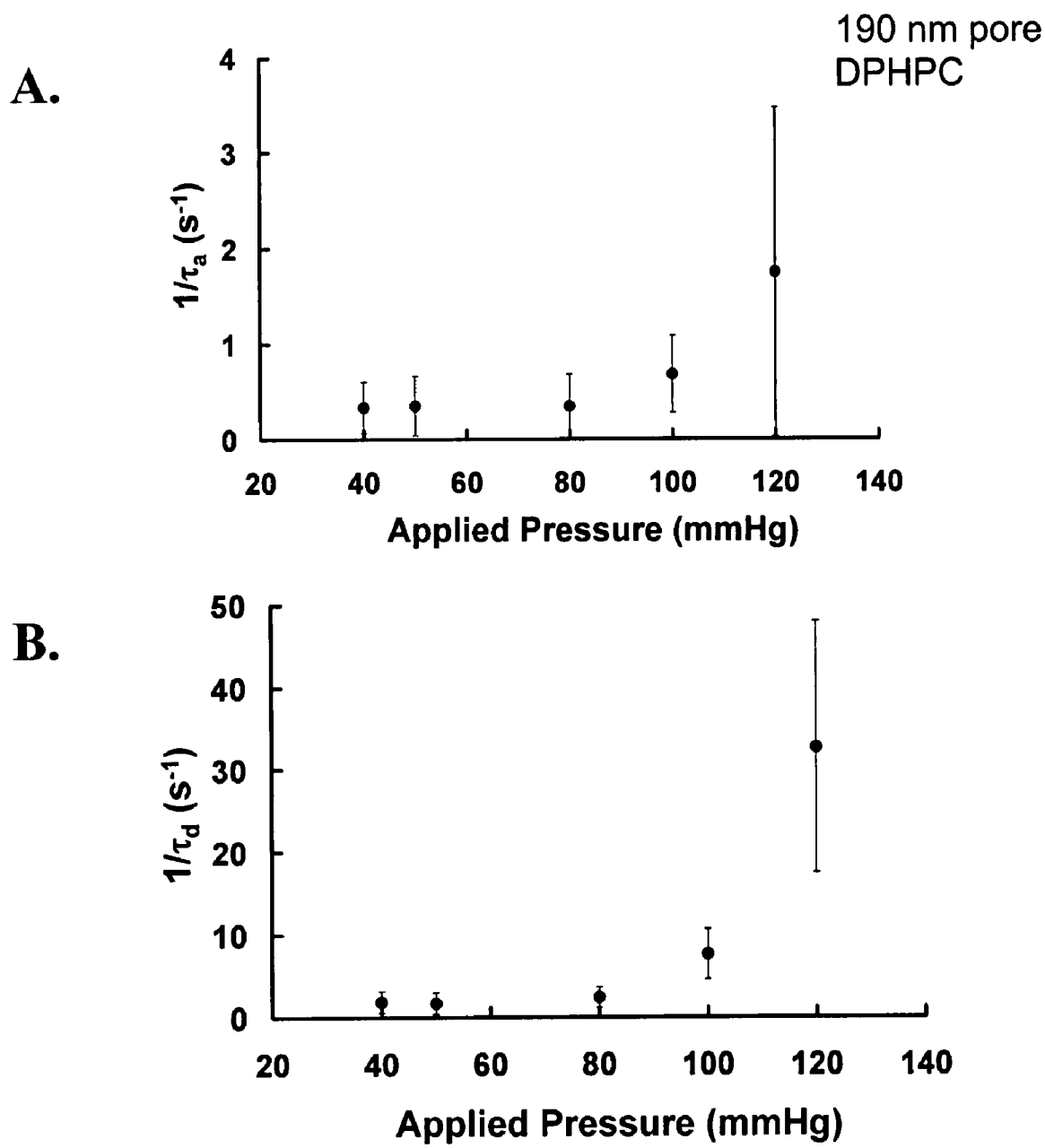
FIG. 16 are two graphs/plots of the rates of insertion ($1/\tau_a$) (upper plot) and desertion ($1/\tau_a$) of $s_7$-βCD (lower plot) as a function of the transmembrane pressure.

FIG. 16 are plots of the rates of insertion ($1/\tau_a$) and desertion ($1/\tau_a$) of $s_7$-βCD as a function of the transmembrane pressure. The data demonstrate that the rate of binding of a single molecule to the protein ion channel may be controlled by varying the transmembrane pressure.

Once the bilayer is formed, the mechanical and electrical stability of the structure can be tested in detail. Traditional planar bilayer and patch clamp measurements require precautions to ensure that the setup is isolated from any vibrations, which include isolation air tables and positioning the experimental setup in the ground floor of a building (Molleman, A. Patch Clamping; Wiley. West Sussex. England, 2003). The glass nanopore membrane, either as a supported lipid bilayer or suspended lipid bilayer structure (FIG. 1(A) or 1(B)) can withstand vigorous solution stirring including for instance removing the capillary from solution, maintaining a water droplet on the end, and inserting the capillary back in solution while keeping the bilayer membrane intact.

Figure 17:
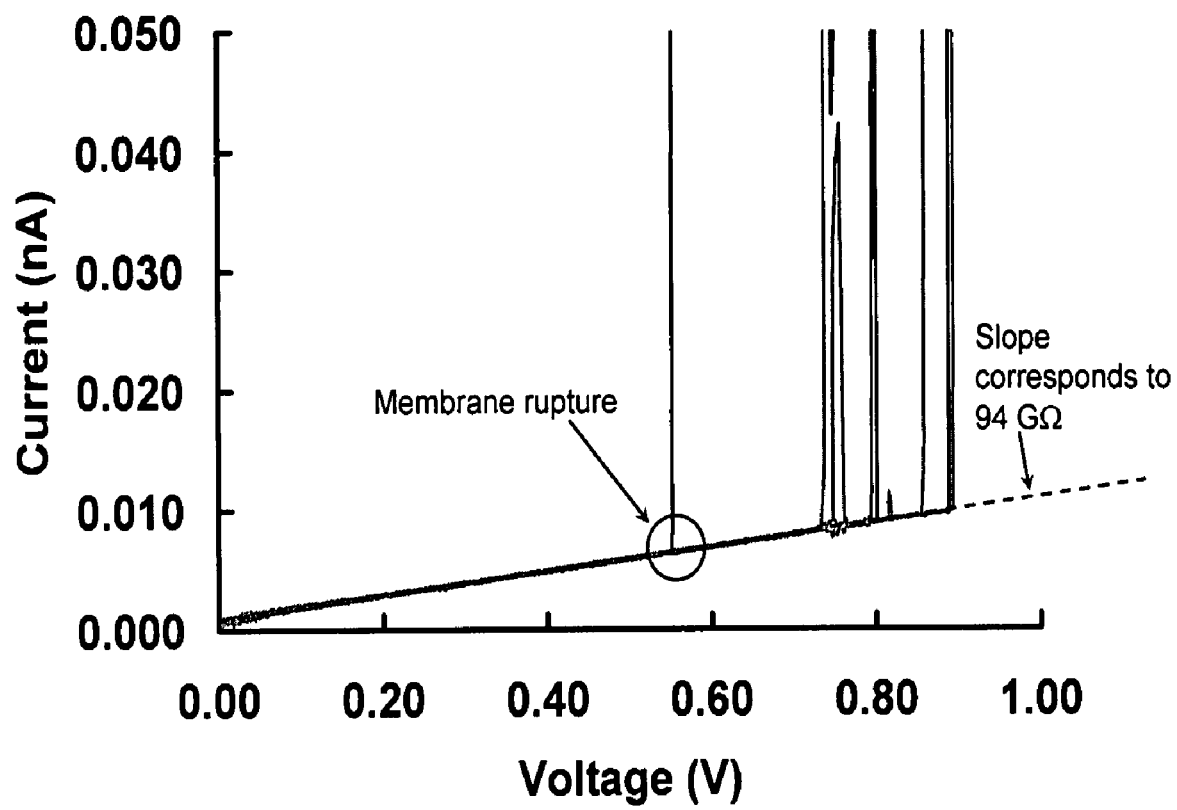
FIG. 17 is a graph showing i-V curves for a spanning lipid bilayer (POPC) showing that the typical breakdown voltage is ~0.8V.

FIG. 17 shows i-V curves for a spanning lipid bilayer (POPC) showing that the typical breakdown voltage is ~0.8V. This experiment is repeatedly achieved on the glass nanopore membrane. This breakdown voltage is significantly higher than the breakdown voltage of ~200-300 mV reported using traditional experimental planar bilayer setup employing, for instance, the TEFLON™ membrane. i-V curves for supported lipid bilayers exhibit typical breakdown voltages is ~2.0V. The unusually high breakdown voltages of the lipid bilayer provide a tremendous advantage in using the glass nanopore membranes in fundamental research and in device applications.

The storage lifetime of bilayers prepared on the glass nanopore membranes is significantly greater than lifetime of bilayers prepared on TEFLON™ or other polymer membranes, exceeding more that 3 weeks. The increased lifetime is due to a combination of factors: the small orifice radius of the glass nanopore membranes; the chemical modification of the glass surface; and the conical shape of the nanopore.

Due to the unusually high voltage stability of the bilayer on the glass nanopore membrane, the invention provides a means to electrostatically trapped molecules that possess electrical charge and/or dipoles, within the channel of a protein that is supported within the lipid bilayer. For instance, an ionic adapter molecule used for enhancing chemical sensing applications of αHL can be electrostatically driven into the protein channel where it remains bound for indefinite periods of time. This ability is specifically applicable to strategies in chemical sensing and DNA sequencing using ion channels devices based on the nanopore membranes due to the achievable high voltage stability of the bilayer.

Using the glass nanopore membrane, charged adapter molecules can be electrostatically trapped for indefinite periods of time (e.g., minutes, hours, days, etc.) inside a protein ion channel by applying a voltage across the lipid bilayer membrane in which the protein ion channel is inserted.

α-HL and other biological and synthetic pores are being developed for use in DNA sequencing. In this application, the DNA is driven through the pore by an electrical voltage. Key known roadblocks are: (1) the fast DNA translocation rate (~1 to 2 μs/base) prevents simple electrical data acquisition and (2) the diameter of the constriction zone in alpha-HL (~1.4 nm) is slightly too large to generate an electrical signature unique to the base as the base passes through the protein. Electrostatic trapping of $s_7$-βCD and other adapter molecules in the lumen of the protein reduces the size of the channel through which the DNA passes, thereby reducing the translocation rate and reducing the size of the constriction zone in which the base signature is generated. This invention potentially removes the major known obstacles in DNA sequencing using ion channels.

An adapter molecule has a molecular structure that allows detection of single molecules. The trapped adapter molecule may have a cyclic structure, e.g., heptakis (6-O-sulfo)-β-cyclodextrin ("$S_7$-βCD"), with a diameter that better matches the diameter of a nucleic acid (e.g., DNA, RNA, or polynucleic acid) than the original protein ion channel. e.g., α-HL, thereby providing a simple means to control the translocation rate of nucleic acid through the protein channel. The method is general and can be applied to adapter molecules and ion channels different from the examples described herein. For instance, electrostatic trapping of adapter molecules in synthetic (or other) pores may be achieved.

Adapter molecules can be synthesized by ordinary chemical methods of nearly any structure and with different functional groups, electrical charge, and electrical dipoles. Thus, an adapter molecule of the precise ideal structure for electrostatic trapping can be designed and synthesized, for the above applications. For instance, commercially available adapters included: alphacyclodextrin-4.7-5.3 Å, β-cyclodextrin-6.0-6.5 Å, γ-cyclodextrin-7.5-8.3 Å, each having a well defined pore diameter. These molecules can be modified to include different charge groups and other functionality.

Figure 18:
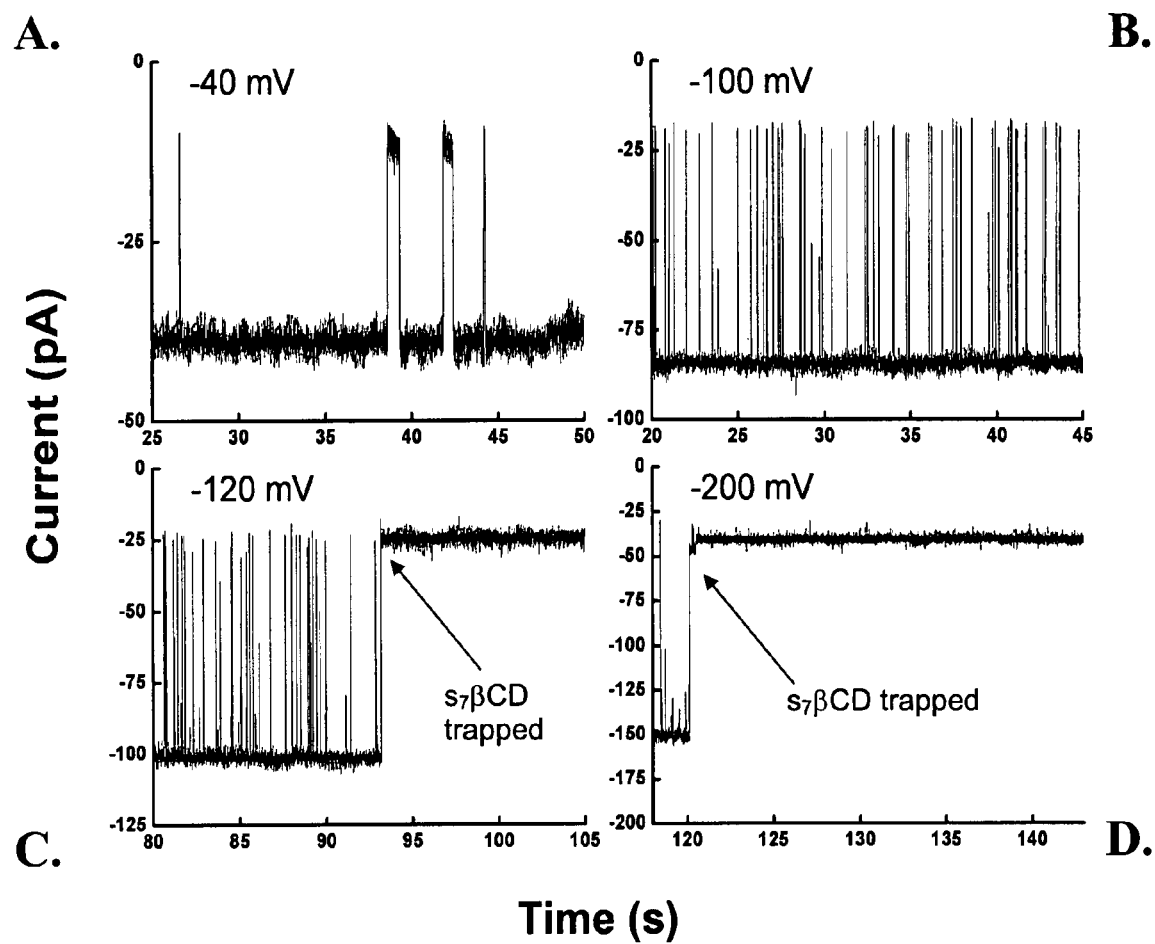
FIG. 18 are four graphs showing the binding of $s_7$-$\beta_{CD}$ to α-HL, inserted into a spanning lipid bilayer (DPhPC) as a function of the transmembrane voltage at constant pressure (~40 mm Hg). The results demonstrate the electrostatic trapping of $s_7$-βCD as a function of voltage across the bilayer. Electrostatic trapping (long-lived binding) of $s_7$-βCD at large negative voltages is evidenced by the steady decrease in current.

FIG. 18 presents graphs demonstrating the electrostatic trapping of $s_7$-βCD. The experiment was performed using a glass nanopore membrane modified with 3-cyanopropyldimetylchlorosilane. The internal nanopore solution was 1 μM α-HL, 1 M KCl, and 10 mM phosphate buffer (PBS pH 7.4). The external solution was 1 M KCl 10 mM PBS (pH 7.4) containing 50 μM $s_7$-βCD. Two Ag/AgCl electrodes were used to bias a potential across the nanopore membrane, with potential referenced to the internal solution. A bilayer composed of 1,2-diphytanoyl-sn-glycero-3-phosphocholine (DPhPC) was painted across the nanopore (450 nm) and a single alpha-HL was inserted into the bilayer membrane. A DC voltage ranging between −40 to −200 mV (trans relative to cis) was applied to monitor the effects of $s_7$-βCD binding events inside the alpha-HL channel as a function of the applied voltage. A positive transmembrane pressure of 40-3 mm Hg was applied to ensure stable protein insertion (FIG. 4). The focus reported herein is the use of high voltages (>−0.1V) to extend the lifetime of $s_7$-βCD within the lumen of the alpha-HL channel. Stable protein insertion occurs over a wide pressure range as demonstrated in FIG. 4.

The results presented in FIG. 18 demonstrate the electrostatic trapping of $s_7$-βCD as a function of voltage in an alpha-HL channel, inserted in a suspended lipid bilayer at the orifice of a nanopore membrane. Stable trapping of $s_7$-βCD at −120 and −200 mV is demonstrated. Specifically, the $s_7$-βCD molecule is trapped for extended periods of time (e.g., hours) at voltages greater than −200V.

The structure, size, and charge of the adapter molecule to be electrostatically trapped may be optimized for different applications, e.g., DNA sequencing. This is a matter of straightforward organic chemistry.

When a potential of −40 mV is applied, reversible stochastic $s_7$-PCD binding events are readily seen with relatively short lifetimes as expected. When a single $s_7$-βCD molecule enters the alpha-HL channel a characteristic drop in current is seen as a consequence of the increased resistance through the channel. An increase of potential to −100 mV causes the stochastic binding events to occur more frequently, but still reversibly Once an applied potential >−120 mV is used, electrostatic trapping of the $s_7$-βCD can be seen. This is shown by the onset of the characteristic current drop associated with $s_7$-βCD entering the channel, without the return to the normal open state of the channel or initial current level. The electrostatic trapping is labeled in the two current-time plots titled −120 mV and −200 mV (FIG. 16) as "enters and stays."

After electrostatic trapping at more negative than −120 mV for an extended period of time (e.g., 10 minute test), the voltage is reduced to release $s_7$-βCD from the alpha-HL channel. The conductivity of the alpha-HL channel is the same before and after electrostatic trapping of s7-βCD demonstrating that the method does not damage or alter the protein.

The foregoing demonstrates that a charged adapter molecule, such as $s_7$-βCD, can be electrostatically trapped for indefinite periods of time (e.g., hours) inside a protein ion channel, e.g., alpha-HL, by applying an electrostatic voltage across the lipid bilayer membrane in which the ion channel is inserted. The trapped adapter molecule has a molecular structure that allows detection of single molecules. The trapped adapter molecule may have a cyclic structure, e.g., s7-βCD, with a diameter that better matches the diameter of a nucleic acid such as DNA than the original protein channel, thereby providing a simple means to control the translocation rate of DNA through the protein channel.

The method is general and can be applied to adapter molecules and ion channels different from the examples described above. For instance, electrostatic trapping of adapter molecules in synthetic pores is possible.

Advantages of this electrostatic trapping method in applications include:

ADVANTAGE 1. Adapter molecules, e.g., beta-cyclodextrin, have been previously used in ion channel recordings, primarily by the Hagan Bayley group at Oxford University. However, the adapter molecules reside temporarily within the barrel or lumen of the protein. For instance, $s_7$-βCD, resides for ~1 sec when a voltage of −0.04 V is applied across the lipid bilayer membrane (trans relative to cis). The molecule then diffuses out of the barrel. This transient binding and unbinding greatly reduces its potential utility in sensor applications. Using the aforementioned glass nanopore membrane much higher transmembrane voltages can be applied. At voltages greater than −0.20 V, s7-βCD is inserted into the lumen of alpha-HL and does not dissociate from the protein until the voltage is reduced below −0.20. Thus, this trapping creates a long-lived α-HL/$s_7$-βCD structure.

ADVANTAGE 2. α-HL and other biological and synthetic pores are proposed for use in DNA sequencing. In such an application, the DNA is driven through the pore by an electrical voltage. Key roadblocks are: (1) the fast DNA translocation rate (~2 μs/base) prevents simple electrical data acquisition and (2) the diameter of the constriction zone in α-HL (~1.4 nm) is slightly too large to generate an electrical signature unique to the base as the base passes through the protein. Electrostatic trapping of $s_7$-βCD and other adapter molecules in the lumen of the protein reduces the size of the channel through which the DNA passes, thereby reducing the translocation rate, and reducing the size of the constriction zone in which the base signature is generated.

Furthermore, adapter molecules can be synthesize by ordinary chemical methods of nearly any structure and with different functional groups, electrical charge, and electrical dipoles. Thus, an adapter molecule of the precise ideal structure for electrostatic trapping cm be designed and synthesized, for the above applications. For instance, commercially available adapters included; alpha-cyclodextrin-4.7-5.3 Angstroms, β-cyclodextrin-6.0-6.5 Angstroms, and gamma-cyclodextrin-7.5-8.3 Angstroms, each having a well defined pore diameter. These molecules can be modified to include charge groups and other functionality.

While this invention has been described in certain embodiments, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

What is claimed is:

1. A nanopore device comprising:
   a membrane having a thickness, with a first, exterior, side and a second, interior, side, the first side being opposite the second side, wherein the membrane is made from a material selected from the group consisting of glass, silicate, ceramic, and combinations thereof;
   at least one nanopore extending through the membrane, thus forming at least one channel connecting the first side and the second side of the membrane, wherein the nanopore has a first opening, a second opening, and a depth, wherein the first opening opens to the first side of the membrane, and the second opening opens to the second side of the membrane, and wherein surface portions of the first side and the at least one channel connecting the first side and the second side of the membrane include modifying molecules defining hydrophobic surfaces; and
   means for spanning across the first opening of the nanopore, wherein the means for spanning across the first opening of the nanopore is a supported lipid bilayer structure or a spanning lipid bilayer structure.

2. The nanopore device of claim 1, wherein the membrane is made from a glass.

3. The nanopore device of claim 1, wherein the nanopore is of a truncated conical shape and wherein a radius of the first opening of the nanopore is smaller than a radius of the second opening of the nanopore.

4. The nanopore device of claim 1, further comprising at least one sensing entity embedded within the means for spanning across the first opening of the nanopore.

5. The nanopore device of claim 4, wherein the sensing entity is selected from the group consisting of a protein ion channel, a modified ion channel, an enzyme, and a biological entity that produces an electrical signal upon interacting with analytes, ions, and molecules in the solution.

6. The nanopore device of claim 5, wherein the sensing entity is a protein ion channel selected from the group consisting of α-hemolysin, an engineered version of α-hemolysin, and porin OmpF.

7. The nanopore device of claim 1, wherein a radius of the first opening of the nanopore ranges from about 2 nm to about 500 nm, or larger.

8. The nanopore device of claim 1, further comprising a pressure apparatus for applying a transmembrane pressure between the first side and the second side of the membrane.

9. The nanopore device of claim 1, wherein the modifying molecules are 3-cyano-propyldimethylchlorosilane or other silanes.

10. The nanopore device of claim 1, further comprising:
    means for applying an electric field across the first side and the second side of the membrane;
    means for monitoring a current flow or resistance through the nanopore; and
    means for processing an observed current flow or resistance to produce a useful output.

11. The nanopore device of claim 10, wherein the means for applying an electric field comprises a first electrode and a second electrode.

12. The nanopore device of claim 11, wherein first electrode is positioned on the first side of the membrane and a second electrode is positioned on the second side of the membrane.

13. The nanopore device of claim 12, wherein the first electrode and the second electrode are made of Ag/AgCl.

14. The nanopore device of claim 1, wherein the thickness of the membrane ranges from about 20 µm to about 75 µm.

15. A method of forming a nanopore device, the method comprising:
    providing a membrane having a thickness, with a first, exterior, side and second, interior, side, the first side being opposite to the second side;
    providing at least one nanopore extending through the membrane over the thickness of the membrane, thus forming at least one channel connecting the first side and the second side of the membrane, wherein the nanopore has a first opening that opens to the first side of the membrane, a second opening that opens to the second side of the membrane, and a depth;
    changing the surface properties of the membrane by creating hydrophobic surface portions along the first side and the at least one channel connecting the first side and the second side of the membrane;
    depositing a first lipid monolayer on a surface portion of the first side of the membrane and a second lipid monolayer on a surface portion of the at least one channel connecting the first side and the second side of the membrane that join together at about the edge of the first opening of the nanopore to form a lipid bilayer spanning across the first opening of the nanopore;
    embedding a sensing entity in the lipid bilayer spanning across the first opening of the nanopore;
    applying an electric field across the first side and the second side of the membrane;
    monitoring a current flow or resistance through the nanopore; and
    processing the observed current flow or resistance to produce a useful output.

16. The method according to claim 15, wherein embedding a sensing entity comprises inserting the sensing entity into the lipid bilayer by applying a transmembrane pressure between the first side and the second side of the membrane.

17. The method according to claim 15, further comprising removing the embedded sensing entity from the lipid bilayer by reducing or removing an applied transmembrane pressure between the first side and the second side of the membrane.

18. The method according to claim 15, further comprising electrostatically trapping adapter molecules with electrical charge or permanent dipoles in the sensing entity.

19. The method according to claim 15, wherein a radius of the first opening of the nanopore ranges from about 2 nm to about 500 nm, or larger.

20. The method according to claim 15, wherein changing the surface properties of the membrane comprises chemically modifying the first and second sides and the at least one channel connecting the first side and the second side of the membrane such that the surface portions of the first and second sides and the at least one channel connecting the first side and the second side of the membrane are rendered hydrophobic.

21. A method for single molecule detection of an analyte using a nanopore device including a membrane having a thickness, with a first, exterior, side and a second, interior, side, the first side being opposite the second side, wherein the membrane is made from a material selected from the group consisting of glass, silicate, ceramic, and combinations thereof; at least one nanopore extending through the membrane, thus forming at least one channel connecting the first side and the second side of the membrane, wherein the nanopore has a first opening, a second opening, and a depth, wherein the first opening opens to the first side of the membrane, and the second opening opens to the second side of the membrane, and wherein surface portions of the first side and the at least one channel connecting the first side and the second side of the membrane include modifying molecules defining hydrophobic surfaces; and means for spanning across the first opening of the nanopore, wherein the means for spanning across the first opening of the nanopore is a supported lipid bilayer structure or a spanning lipid bilayer structure, the method comprising:
    providing a sample solution containing an analyte of interest;
    contacting the nanopore device with the sample solution such that the first, exterior, side of the membrane is immersed in the sample solution and the at least one nanopore is filled with the sample solution;
    applying an appropriate voltage across the first and second side of the membrane;
    measuring the resistance or current flow through the at least one nanopore using either alternating current (AC) or direct current (DC) measurements; and
    analyzing the observed resistance or current flow to produce a useful output.

22. The method according to claim 21, wherein the sensing device further comprises a sensing entity embedded in the lipid bilayer structure spanning across the first opening of the nanopore, and wherein the sensing entity of the nanopore device is a drug target or a modified drug target, the analyte of interest is a drug candidate and the useful output is the binding affinity of the drug candidate with the drug target or modified drug candidate.

23. The method according to claim 22, wherein the sensing entity of the nanopore device recognizes specific nucleotides, the analyte of interest is a nucleic acid and the useful output is sequence information of the nucleic acid.

* * * * *